(12) United States Patent
Siliciano et al.

(10) Patent No.: US 7,468,274 B2
(45) Date of Patent: Dec. 23, 2008

(54) SINGLE CELL ANALYSIS OF HIV REPLICATION CAPACITY AND DRUG RESISTANCE

(75) Inventors: Robert Siliciano, Baltimore, MD (US); Haili Zhang, Stanford, CA (US); Yan Zhou, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 253 days.

(21) Appl. No.: 11/042,988

(22) Filed: Jan. 25, 2005

(65) Prior Publication Data
US 2005/0244818 A1    Nov. 3, 2005

Related U.S. Application Data

(60) Provisional application No. 60/540,716, filed on Jan. 30, 2004.

(51) Int. Cl.
*C12N 15/867*    (2006.01)

(52) U.S. Cl. .................. 435/320.1; 435/235.1; 435/366
(58) Field of Classification Search ...................... None
See application file for complete search history.

(56) References Cited

OTHER PUBLICATIONS

Akari et al., Journal of General Virology, vol. 80, 1999, pp. 2945-2949.*

* cited by examiner

*Primary Examiner*—James S Ketter
(74) *Attorney, Agent, or Firm*—Edwards Angell Palmer & Dodge LLP; Peter F. Corless; Jonathan M. Sparks

(57) ABSTRACT

A novel single-cell-level phenotypic assay is described, which can simultaneously analyze HIV-1 drug susceptibility and intrinsic replication capacity. This allows quantitative dissection of the functions of antiretroviral drugs into suppression of viral replication and selection of resistant viruses with diminished replication capacities. The disclosed assay provides a tool for the rational evaluation of treatment decisions for patients failing antiretroviral therapy and is expected to be an important part in clinical management of HIV.

21 Claims, 5 Drawing Sheets

SEQUENCE LISTING

```
<160> NUMBER OF SEQ ID NOS: 16

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
attgggtacc tgtcgccacc atggtgagc                                            29
```

<210> SEQ ID NO 2
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtccgtgcta gcttacagct cgtccttgta cagctcgtcc atgcc            45

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcaagagttt tggctgaagc aatgag                                 26

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccttgcccct gcttctgtat ttctgc                                 26

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgcagggccc ctaggaaaaa gggctg                                 26

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
catgtaccgg ttcttttaga atctctctgt t                           31

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cagaaaggca attttaggaa cc                                     22

<210> SEQ ID NO 8

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
acctacacct gtcaacataa ttgg                                              24

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gataaatttg atatgtccat tg                                                22

<210> SEQ ID NO 10
<211> LENGTH: 9719
<212> TYPE: DNA
<213> ORGANISM: Human immunodeficiency virus type 1

<400> SEQUENCE: 10
tggaagggct aattcactcc caacgaagac aagatatcct tgatctgtgg atctaccaca        60
cacaaggcta cttccctgat tagcagaact acacaccagg gccagggatc agatatccac       120
tgacctttgg atggtgctac aagctagtac cagttgagcc agagaagtta agaagaagcca      180 acaaaggaga gaacaccagc ttgttacacc ctgtgagcct gcatggaatg gatgacccgg       240
agagagaagt gttagagtgg aggtttgaca gccgcctagc atttcatcac atggcccgag       300
agctgcatcc ggagtacttc aagaactgct gacatcgagc ttgctacaag ggactttccg       360
ctggggactt tccagggagg cgtggcctgg gcgggactgg ggagtggcga gccctcagat       420
cctgcatata agcagctgct ttttgcctgt actgggtctc tctggttaga ccagatctga       480
gcctgggagc tctctggcta actagggaac ccactgctta agcctcaata aagcttgcct       540
tgagtgcttc aagtagtgtg tgcccgtctg ttgtgtgact ctggtaacta gagatccctc       600 agacccttt agtcagtgtg aaaatctct agcagtggcg cccgaacagg gacctgaaag        660
cgaaagggaa accagaggag ctctctcgac gcaggactcg gcttgctgaa gcgcgcacgg       720
caagaggcga gggcggcga ctggtgagta cgccaaaaat tttgactagc ggaggctaga       780
aggagagaga tgggtgcgag agcgtcagta ttaagcgggg gagaattaga tcgatgggaa       840
aaaattcggt taaggccagg gggaaagaaa aatataaat taaaacatat agtatgggca       900
agcagggagc tagaacgatt cgcagttaat cctggcctgt tagaaacatc agaaggctgt       960
agacaaatac tgggacagct acaaccatcc cttcagacag gatcagaaga acttagatca      1020
ttatataata cagtagcaac cctctattgt gtgcatcaaa ggatagagat aaaagacacc      1080
aaggaagctt tagacaagat agaggaagag caaaacaaaa gtaagaaaaa agcacagcaa      1140
gcagcagctg acacaggaca cagcaatcag gtcagccaaa attaccctat agtgcagaac      1200
atccaggggc aaatggtaca tcaggccata tcacctagaa ctttaaatgc atgggtaaaa      1260
gtagtagaag agaaggcttt cagcccagaa gtgatacccc tgttttcagc attatcagaa      1320
ggagccaccc cacaagattt aaacaccatg ctaaacacag tggggggaca tcaagcagcc      1380
atgcaaatgt taaaagagac catcaatgag gaagctgcag aatgggatag agtgcatcca      1440
```

| | |
|---|---|
| gtgcatgcag ggcctattgc accaggccag atgagagaac caaggggaag tgacatagca | 1500 |
| ggaactacta gtacccttca ggaacaaata ggatggatga caaataatcc acctatccca | 1560 |
| gtaggagaaa tttataaaag atggataatc ctgggattaa ataaaatagt aagaatgtat | 1620 |
| agccctacca gcattctgga cataagacaa ggaccaaagg aaccctttag agactatgta | 1680 |
| gaccggttct ataaaactct aagagccgag caagcttcac aggaggtaaa aaattggatg | 1740 |
| acagaaacct tgttggtcca aaatgcgaac ccagattgta agactatttt aaaagcattg | 1800 |
| ggaccagcgg ctacactaga agaaatgatg acagcatgtc agggagtagg aggacccggc | 1860 |
| cataaggcaa gagttttggc tgaagcaatg agccaagtaa caaattcagc taccataatg | 1920 |
| atgcagagag gcaattttag gaaccaaaga aagattgtta agtgtttcaa ttgtggcaaa | 1980 |
| gaagggcaca cagccagaaa ttgcagggcc cctaggaaaa agggctgttg gaaatgtgga | 2040 |
| aaggaaggac accaaatgaa agattgtact gagagacagg ctaattttttt agggaagatc | 2100 |
| tggccttcct acaagggaag gccagggaat tttcttcaga gcagaccaga gccaacagcc | 2160 |
| ccaccagaag agagcttcag gtctggggta gagacaacaa ctccccctca gaagcaggag | 2220 |
| ccgatagaca aggaactgta tcctttaact tccctcaggt cactctttgg caacgacccc | 2280 |
| tcgtcacaat aaagataggg gggcaactaa aggaagctct attagataca ggagcagatg | 2340 |
| atacagtatt agaagaaatg agtttgccag gaagatggaa accaaaaatg ataggggaa | 2400 |
| ttggaggttt tatcaaagta agacagtatg atcagatact catagaaatc tgtggacata | 2460 |
| aagctatagg tacagtatta gtaggaccta cacctgtcaa cataattgga agaaatctgt | 2520 |
| tgactcagat tggttgcact ttaaatttttc ccattagccc tattgagact gtaccagtaa | 2580 |
| aattaaagcc aggaatggat ggcccaaaag ttaaacaatg gccattgaca gaagaaaaaa | 2640 |
| taaaagcatt agtagaaatt tgtacagaga tggaaaagga agggaaaatt tcaaaaattg | 2700 |
| ggcctgaaaa tccatacaat actccagtat ttgccataaa gaaaaagac agtactaaat | 2760 |
| ggagaaaatt agtagatttc agagaactta ataagagaac tcaagacttc tgggaagttc | 2820 |
| aattaggaat accacatccc gcagggttaa aaagaaaaa atcagtaaca gtactggatg | 2880 |
| tgggtgatgc atattttttca gttcccttag atgaagactt caggaagtat actgcattta | 2940 |
| ccatacctag tataaacaat gagacaccag ggattagata tcagtacaat gtgcttccac | 3000 |
| agggatggaa aggatcacca gcaatattcc aaagtagcat gacaaaaatc ttagagcctt | 3060 |
| ttagaaaaca aaatccagac atagttatct atcaatacat ggatgatttg tatgtaggat | 3120 |
| ctgacttaga aatagggcag catagaacaa aaatagagga gctgagacaa catctgttga | 3180 |
| ggtgggggact taccacacca gacaaaaaac atcagaaaga acctccattc ctttggatgg | 3240 |
| gttatgaact ccatcctgat aaatggacag tacagcctat agtgctgcca gaaaaagaca | 3300 |
| gctggactgt caatgacata cagaagttag tggggaaatt gaattgggca agtcagattt | 3360 |
| acccagggat taaagtaagg caattatgta aactccttag aggaaccaaa gcactaacag | 3420 |
| aagtaatacc actaacagaa gaagcagagc tagaactggc agaaaacaga gagattctaa | 3480 |
| aagaaccagt acatggagtg tattatgacc catcaaaaga cttaatagca gaaatacaga | 3540 |
| agcaggggca aggccaatgg acatatcaaa tttatcaaga gccatttaaa aatctgaaaa | 3600 |
| caggaaaata tgcaagaatg aggggtgccc acactaatga tgtaaaacaa ttaacagagg | 3660 |
| cagtgcaaaa aataaccaca gaaagcatag taatatgggg aaagactcct aaatttaaac | 3720 |
| tgcccataca aaaggaaaca tgggaaacat ggtggacaga gtattggcaa gccacctgga | 3780 |

```
ttcctgagtg ggagtttgtt aatacccctc ccttagtgaa attatggtac cagttagaga    3840
aagaacccat agtaggagca gaaaccttct atgtagatgg ggcagctaac agggagacta    3900
aattaggaaa agcaggatat gttactaata gaggaagaca aaaagttgtc accctaactg    3960
acacaacaaa tcagaagact gagttacaag caatttatct agctttgcag gattcgggat    4020
tagaagtaaa catagtaaca gactcacaat atgcattagg aatcattcaa gcacaaccag    4080
atcaaagtga atcagagtta gtcaatcaaa taatagagca gttaataaaa aaggaaaagg    4140
tctatctggc atgggtacca gcacacaaag gaattggagg aaatgaacaa gtagataaat    4200
tagtcagtgc tggaatcagg aaagtactat ttttagatgg aatagataag gcccaagatg    4260
aacatgagaa atatcacagt aattggagag caatggctag tgattttaac ctgccacctg    4320
tagtagcaaa agaaatagta gccagctgtg ataaatgtca gctaaaagga gaagccatgc    4380
atggacaagt agactgtagt ccaggaatat ggcaactaga ttgtacacat ttagaaggaa    4440
aagttatcct ggtagcagtt catgtagcca gtggatatat agaagcagaa gttattccag    4500
cagaaacagg gcaggaaaca gcatattttc ttttaaaatt agcaggaaga tggccagtaa    4560
aaacaataca tactgacaat ggcagcaatt tcaccggtgc tacggttagg gccgcctgtt    4620
ggtgggcggg aatcaagcag gaatttggaa ttccctacaa tccccaaagt caaggagtag    4680
tagaatctat gaataaagaa ttaagaaaaa ttataggaca ggtaagagat caggctgaac    4740
atcttaagac agcagtacaa atggcagtat tcatccacaa ttttaaaaga aaggggggga    4800
ttggggggta cagtgcaggg gaaagaatag tagacataat agcaacagac atacaaacta    4860
aagaattaca aaaacaaatt acaaaaattc aaaattttcg ggtttattac agggacagca    4920
gaaatccact ttggaaagga ccagcaaagc tcctctggaa aggtgaaggg gcagtagtaa    4980
tacaagataa tagtgacata aaagtagtgc caagaagaaa agcaaagatc attagggatt    5040
atggaaaaca gatggcaggt gatgattgtg tggcaagtag acaggatgag gattagaaca    5100
tggaaaagtt tagtaaaaca ccatatgtat gtttcaggga agctagggga tggttttat     5160 agacatcact atgaaagccc tcatccaaga ataagttcag aagtacacat cccactaggg    5220
gatgctagat tggtaataac aacatattgg ggtctgcata caggagaaag agactggcat    5280
ttgggtcagg gagtctccat agaatggagg aaaaagagat atagcacaca agtagaccct    5340
gaactagcag accaactaat tcatctgtat tactttgact gtttttcaga ctctgctata    5400
agaaaggcct tattaggaca catagttagc cctaggtgtg aatatcaagc aggacataac    5460
aaggtaggat ctctacaata cttggcacta gcagcattaa taacaccaaa aaagataaag    5520
ccacctttgc ctagtgttac gaaactgaca gaggatagat ggaacaagcc ccagaagacc    5580
aagggccaca gagggagcca cacaatgaat ggacactaga gcttttagag gagcttaaga    5640
atgaagctgt tagacatttt cctaggattt ggctccatgg cttagggcaa catatctatg    5700
aaacttatgg ggatacttgg gcaggagtgg aagccataat aagaattctg caacaactgc    5760
tgtttatcca ttttcagaat tgggtgtcga catagcagaa taggcgttac tcgacagagg    5820
agagcaagaa atggagccag tagatcctag actagagccc tggaagcatc caggaagtca    5880
gcctaaaact gcttgtacca attgctattg taaaaagtgt tgctttcatt gccaagtttg    5940
tttcataaca aaagccttag gcatctccta tggcaggaag aagcggagac agcgacgaag    6000
agctcatcag aacagtcaga ctcatcaagc ttctctatca aagcagtaag tagtacatgt    6060
aacgcaacct ataccaatag tagcaatagt agcattagta gtagcaataa taatagcaat    6120
agttgtgtgg tccatagtaa tcatagaata taggaaaata ttaagacaaa gaaaaataga    6180
```

```
caggttaatt gatagactaa tagaaagagc agaagacagt ggcaatgaga gtgaaggaga    6240
aatatcagca cttgtggaga tgggggtgga gatggggcac catgctcctt gggatgttga    6300
tgatctgtag tgctacagaa aaattgtggg tcacagtcta ttatgggta cctgtgtgga    6360 aggaagcaac caccactcta ttttgtgcat cagatgctaa agcatatgat acagaggtac    6420
ataatgtttg ggccacacat gcctgtgtac ccacagaccc caaccccacaa gaagtagtat    6480 tggtaaatgt gacagaaaat tttaacatgt ggaaaaatga catggtagaa cagatgcatg    6540
aggatataat cagtttatgg gatcaaagcc taaagccatg tgtaaaatta accccactct    6600
gtgttagttt aaagtgcact gatttgaaga atgatactaa taccaatagt agtagcggga    6660
gaatgataat ggagaaagga gagataaaaa actgctcttt caatatcagc acaagcataa    6720
gaggtaaggt gcagaaagaa tatgcatttt tttataaact tgatataata ccaatagata    6780
atgatactac cagctataag ttgacaagtt gtaacacctc agtcattaca caggcctgtc    6840
caaaggtatc ctttgagcca attcccatac attattgtgc cccggctggt tttgcgattc    6900
taaaatgtaa taataagacg ttcaatgaaa caggaccatg tacaaatgtc agcacagtac    6960
aatgtacaca tggaattagg ccagtagtat caactcaact gctgttaaat ggcagtctag    7020
cagaagaaga ggtagtaatt agatctgtca atttcacgga caatgctaaa accataatag    7080
tacagctgaa cacatctgta gaattaatt gtacaagacc caacaacaat acaagaaaaa    7140
gaatccgtat ccagagagga ccagggagag catttgttac aataggaaaa ataggaaata    7200
tgagacaagc acattgtaac attagtgagc aaaatggaa taacactttta aaacagatag    7260 ctagcaaatt aagagaacaa tttggaaata taaaacaat aatctttaag caatcctcag    7320
gaggggaccc agaaattgta acgcacagtt ttaattgtgg aggggaattt ttctactgta    7380
attcaacaca actgtttaat agtacttggt ttaatagtac ttggagtact gaagggtcaa    7440
ataacactga aggaagtgac acaatcaccc tcccatgcag aataaaacaa attataaaca    7500
tgtggcagaa agtaggaaaa gcaatgtatg cccctcccat cagtggacaa attagatgtt    7560
catcaaatat tacagggctg ctattaacaa gagatggtgg taatagcaac aatgagtccg    7620
agatcttcag acctggagga ggagatatga gggacaattg gagaagtgaa ttatataaat    7680
ataaagtagt aaaaattgaa ccattaggag tagcacccac caaggcaaag agaagagtgg    7740
tgcagagaga aaaaagagca gtgggaatag gagctttgtt ccttgggttc ttgggagcag    7800
caggaagcac tatgggcgca gcctcaatga cgctgacggt acaggccaga caattattgt    7860
ctggtatagt gcagcagcag aacaatttgc tgagggctat tgaggcgcaa cagcatctgt    7920
tgcaactcac agtctggggc atcaagcagc tccaggcaag aatcctggct gtggaaagat    7980
acctaaagga tcaacagctc ctggggattt ggggttgctc tggaaaactc atttgcacca    8040
ctgctgtgcc ttggaatgct agttggagta ataaatctct ggaacagatt tggaatcaca    8100
cgacctggat ggagtgggac agagaaatta acaattacac aagcttaata cactccttaa    8160
ttgaagaatc gcaaaaccag caagaaaaga atgaacaaga attattggaa ttagataaat    8220
gggcaagttt gtggaattgg tttaacataa caaattggct gtggtatata aaattattca    8280
taatgatagt aggaggcttg gtaggtttaa gaatagtttt tgctgtactt tctatagtga    8340
atagagttag gcagggatat tcaccattat cgtttcagac ccacctccca accccgaggg    8400
gacccgacag gcccgaagga atagaagaag aaggtggaga gagagacaga gacagatcca    8460
ttcgattagt gaacggatcc ttggcactta tctgggacga tctgcggagc ctgtgcctct    8520
```

-continued

```
tcagctacca ccgcttgaga gacttactct tgattgtaac gaggattgtg gaacttctgg    8580
gacgcagggg gtgggaagcc ctcaaatatt ggtggaatct cctacagtat tggagtcagg    8640
aactaaagaa tagtgctgtt agcttgctca atgccacagc catagcagta gctgagggga    8700 cagataggt tatagaagta gtacaaggag cttgtagagc tattcgccac ataccctagaa    8760 gaataagaca gggcttggaa aggatttttgc tataagatgg gtggcaagtg gtcaaaaagt    8820
agtgtgattg gatggcctac tgtaaggaa agaatgagac gagctgagcc agcagcagat    8880
agggtgggag cagcatctcg agacctggaa aaacatggag caatcacaag tagcaataca    8940
gcagctacca atgctgcttg tgcctggcta aagcacaag aggaggagga ggtgggtttt    9000
ccagtcacac ctcaggtacc tttaagacca atgacttaca aggcagctgt agatcttagc    9060 cacttttaa aagaaaaggg gggactggaa gggctaattc actcccaaag aagacaagat    9120
atccttgatc tgtggatcta ccacacacaa ggctacttcc ctgattagca gaactacaca    9180
ccagggccag gggtcagata tccactgacc tttggatggt gctacaagct agtaccagtt    9240
gagccagata agatagaaga ggccaataaa ggagagaaca ccagcttgtt acaccctgtg    9300
agcctgcatg gatgatga cccggagaga gaagtgttag agtggaggtt tgacagccgc    9360 ctagcattc atcacgtggc ccgagagctg catccggagt acttcaagaa ctgctgacat    9420
cgagcttgct acaagggact ttccgctggg actttccag ggaggcgtgg cctgggcggg    9480
actggggagt ggcgagccct cagatcctgc atataagcag ctgctttttg cctgtactgg    9540
gtctctctgg ttagaccaga tctgagcctg ggagctctct ggctaactag ggaacccact    9600
gcttaagcct caataaagct tgccttgagt gcttcaagta gtgtgtgccc gtctgttgtg    9660
tgactctggt aactagagat ccctcagacc ctttagtca gtgtggaaaa tctctagca    9719
```

```
<210> SEQ ID NO 11
<211> LENGTH: 500
<212> TYPE: PRT
<213> ORGANISM: Human immunodeficiency virus type 1

<400> SEQUENCE: 11

Met Gly Ala Arg Ala Ser Val Leu Ser Gly Gly Glu Leu Asp Arg Trp
  1               5                  10                  15

Glu Lys Ile Arg Leu Arg Pro Gly Gly Lys Lys Lys Tyr Lys Leu Lys
             20                  25                  30

His Ile Val Trp Ala Ser Arg Glu Leu Glu Arg Phe Ala Val Asn Pro
         35                  40                  45

Gly Leu Leu Glu Thr Ser Glu Gly Cys Arg Gln Ile Leu Gly Gln Leu
     50                  55                  60

Gln Pro Ser Leu Gln Thr Gly Ser Glu Glu Leu Arg Ser Leu Tyr Asn
 65                  70                  75                  80

Thr Val Ala Thr Leu Tyr Cys Val His Gln Arg Ile Glu Ile Lys Asp
                 85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Asn Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
```

```
            165                 170                 175
Glu Gly Ala Thr Pro Gln Asp Leu Asn Thr Met Leu Asn Thr Val Gly
        180                 185                 190

Gly His Gln Ala Ala Met Gln Met Leu Lys Glu Thr Ile Asn Glu Glu
    195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Arg Gly Asn Phe Arg
    370                 375                 380

Asn Gln Arg Lys Ile Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Tyr Lys Gly Arg Pro Gly Asn Phe
        435                 440                 445

Leu Gln Ser Arg Pro Glu Pro Thr Ala Pro Glu Glu Ser Phe Arg
    450                 455                 460

Ser Gly Val Glu Thr Thr Thr Pro Pro Gln Lys Gln Glu Pro Ile Asp
465                 470                 475                 480

Lys Glu Leu Tyr Pro Leu Thr Ser Leu Arg Ser Leu Phe Gly Asn Asp
                485                 490                 495

Pro Ser Ser Gln
            500

<210> SEQ ID NO 12
<211> LENGTH: 912
<212> TYPE: PRT
<213> ORGANISM: Human immunodeficiency virus type 1

<400> SEQUENCE: 12

Met Ser Leu Pro Gly Arg Trp Lys Pro Lys Met Ile Gly Gly Ile Gly
 1               5                  10                  15

Gly Phe Ile Lys Val Arg Gln Tyr Asp Gln Ile Leu Ile Glu Ile Cys
            20                  25                  30
```

-continued

```
Gly His Lys Ala Ile Gly Thr Val Val Gly Pro Thr Val Asn
        35                  40                  45
Ile Ile Gly Arg Asn Leu Leu Thr Gln Ile Gly Cys Thr Leu Asn Phe
50                      55                  60
Pro Ile Ser Pro Ile Glu Thr Val Pro Val Lys Leu Lys Pro Gly Met
65                      70                  75                  80
Asp Gly Pro Lys Val Lys Gln Trp Pro Leu Thr Glu Glu Lys Ile Lys
                85                  90                  95
Ala Leu Val Glu Ile Cys Thr Glu Met Glu Lys Glu Gly Lys Ile Ser
            100                 105                 110
Lys Ile Gly Pro Glu Asn Pro Tyr Asn Thr Pro Val Phe Ala Ile Lys
            115                 120                 125
Lys Lys Asp Ser Thr Lys Trp Arg Lys Leu Val Asp Phe Arg Glu Leu
        130                 135                 140
Asn Lys Arg Thr Gln Asp Phe Trp Glu Val Gln Leu Gly Ile Pro His
145                 150                 155                 160
Pro Ala Gly Leu Lys Lys Lys Ser Val Thr Val Leu Asp Val Gly
                165                 170                 175
Asp Ala Tyr Phe Ser Val Pro Leu Asp Glu Asp Phe Arg Lys Tyr Thr
            180                 185                 190
Ala Phe Thr Ile Pro Ser Ile Asn Asn Glu Thr Pro Gly Ile Arg Tyr
        195                 200                 205
Gln Tyr Asn Val Leu Pro Gln Gly Trp Lys Gly Ser Pro Ala Ile Phe
    210                 215                 220
Gln Ser Ser Met Thr Lys Ile Leu Glu Pro Phe Arg Lys Gln Asn Pro
225                 230                 235                 240
Asp Ile Val Ile Tyr Gln Tyr Met Asp Asp Leu Tyr Val Gly Ser Asp
                245                 250                 255
Leu Glu Ile Gly Gln His Arg Thr Lys Ile Glu Glu Leu Arg Gln His
            260                 265                 270
Leu Leu Arg Trp Gly Leu Thr Thr Pro Asp Lys Lys His Gln Lys Glu
        275                 280                 285
Pro Pro Phe Leu Trp Met Gly Tyr Glu Leu His Pro Asp Lys Trp Thr
    290                 295                 300
Val Gln Pro Ile Val Leu Pro Glu Lys Asp Ser Trp Thr Val Asn Asp
305                 310                 315                 320
Ile Gln Lys Leu Val Gly Lys Leu Asn Trp Ala Ser Gln Ile Tyr Pro
                325                 330                 335
Gly Ile Lys Val Arg Gln Leu Cys Lys Leu Leu Arg Gly Thr Lys Ala
            340                 345                 350
Leu Thr Glu Val Ile Pro Leu Thr Glu Glu Ala Glu Leu Glu Leu Ala
        355                 360                 365
Glu Asn Arg Glu Ile Leu Lys Glu Pro Val His Gly Val Tyr Tyr Asp
    370                 375                 380
Pro Ser Lys Asp Leu Ile Ala Glu Ile Gln Lys Gln Gly Gln Gly Gln
385                 390                 395                 400
Trp Thr Tyr Gln Ile Tyr Gln Glu Pro Phe Lys Asn Leu Lys Thr Gly
                405                 410                 415
Lys Tyr Ala Arg Met Arg Gly Ala His Thr Asn Asp Val Lys Gln Leu
            420                 425                 430
Thr Glu Ala Val Gln Lys Ile Thr Thr Glu Ser Ile Val Ile Trp Gly
        435                 440                 445
Lys Thr Pro Lys Phe Lys Leu Pro Ile Gln Lys Glu Thr Trp Glu Thr
```

```
            450              455              460
Trp Trp Thr Glu Tyr Trp Gln Ala Thr Trp Ile Pro Glu Trp Glu Phe
465              470              475              480

Val Asn Thr Pro Pro Leu Val Lys Leu Trp Tyr Gln Leu Glu Lys Glu
                 485              490              495

Pro Ile Val Gly Ala Glu Thr Phe Tyr Val Asp Gly Ala Ala Asn Arg
                 500              505              510

Glu Thr Lys Leu Gly Lys Ala Gly Tyr Val Thr Asn Arg Gly Arg Gln
            515              520              525

Lys Val Val Thr Leu Thr Asp Thr Thr Asn Gln Lys Thr Glu Leu Gln
            530              535              540

Ala Ile Tyr Leu Ala Leu Gln Asp Ser Gly Leu Glu Val Asn Ile Val
545              550              555              560

Thr Asp Ser Gln Tyr Ala Leu Gly Ile Ile Gln Ala Gln Pro Asp Gln
                 565              570              575

Ser Glu Ser Glu Leu Val Asn Gln Ile Ile Glu Gln Leu Ile Lys Lys
                 580              585              590

Glu Lys Val Tyr Leu Ala Trp Val Pro Ala His Lys Gly Ile Gly Gly
            595              600              605

Asn Glu Gln Val Asp Lys Leu Val Ser Ala Gly Ile Arg Lys Val Leu
            610              615              620

Phe Leu Asp Gly Ile Asp Lys Ala Gln Asp Glu His Glu Lys Tyr His
625              630              635              640

Ser Asn Trp Arg Ala Met Ala Ser Asp Phe Asn Leu Pro Pro Val Val
                 645              650              655

Ala Lys Glu Ile Val Ala Ser Cys Asp Lys Cys Gln Leu Lys Gly Glu
                 660              665              670

Ala Met His Gly Gln Val Asp Cys Ser Pro Gly Ile Trp Gln Leu Asp
            675              680              685

Cys Thr His Leu Glu Gly Lys Val Ile Leu Val Ala Val His Val Ala
            690              695              700

Ser Gly Tyr Ile Glu Ala Glu Val Ile Pro Ala Glu Thr Gly Gln Glu
705              710              715              720

Thr Ala Tyr Phe Leu Leu Lys Leu Ala Gly Arg Trp Pro Val Lys Thr
                 725              730              735

Ile His Thr Asp Asn Gly Ser Asn Phe Thr Gly Ala Thr Val Arg Ala
                 740              745              750

Ala Cys Trp Trp Ala Gly Ile Lys Gln Glu Phe Gly Ile Pro Tyr Asn
            755              760              765

Pro Gln Ser Gln Gly Val Val Glu Ser Met Asn Lys Glu Leu Lys Lys
            770              775              780

Ile Ile Gly Gln Val Arg Asp Gln Ala Glu His Leu Lys Thr Ala Val
785              790              795              800

Gln Met Ala Val Phe Ile His Asn Phe Lys Arg Lys Gly Gly Ile Gly
                 805              810              815

Gly Tyr Ser Ala Gly Glu Arg Ile Val Asp Ile Ile Ala Thr Asp Ile
                 820              825              830

Gln Thr Lys Glu Leu Gln Lys Gln Ile Thr Lys Ile Gln Asn Phe Arg
            835              840              845

Val Tyr Tyr Arg Asp Ser Arg Asn Pro Leu Trp Lys Gly Pro Ala Lys
            850              855              860

Leu Leu Trp Lys Gly Glu Gly Ala Val Val Ile Gln Asp Asn Ser Asp
865              870              875              880
```

-continued

Ile Lys Val Val Pro Arg Arg Lys Ala Lys Ile Ile Arg Asp Tyr Gly
            885                 890                 895
Lys Gln Met Ala Gly Asp Asp Cys Val Ala Ser Arg Gln Asp Glu Asp
            900                 905                 910

<210> SEQ ID NO 13
<211> LENGTH: 856
<212> TYPE: PRT
<213> ORGANISM: Human immunodeficiency virus type 1

<400> SEQUENCE: 13

Met Arg Val Lys Glu Lys Tyr Gln His Leu Trp Arg Trp Gly Trp Arg
  1               5                  10                  15
Trp Gly Thr Met Leu Leu Gly Met Leu Met Ile Cys Ser Ala Thr Glu
             20                  25                  30
Lys Leu Trp Val Thr Val Tyr Tyr Gly Val Pro Val Trp Lys Glu Ala
         35                  40                  45
Thr Thr Thr Leu Phe Cys Ala Ser Asp Ala Lys Ala Tyr Asp Thr Glu
 50                  55                  60
Val His Asn Val Trp Ala Thr His Ala Cys Val Pro Thr Asp Pro Asn
 65                  70                  75                  80
Pro Gln Glu Val Val Leu Val Asn Val Thr Glu Asn Phe Asn Met Trp
             85                  90                  95
Lys Asn Asp Met Val Glu Gln Met His Glu Asp Ile Ile Ser Leu Trp
            100                 105                 110
Asp Gln Ser Leu Lys Pro Cys Val Lys Leu Thr Pro Leu Cys Val Ser
        115                 120                 125
Leu Lys Cys Thr Asp Leu Lys Asn Asp Thr Asn Thr Asn Ser Ser Ser
130                 135                 140
Gly Arg Met Ile Met Glu Lys Gly Glu Ile Lys Asn Cys Ser Phe Asn
145                 150                 155                 160
Ile Ser Thr Ser Ile Arg Gly Lys Val Gln Lys Glu Tyr Ala Phe Phe
                165                 170                 175
Tyr Lys Leu Asp Ile Ile Pro Ile Asp Asn Asp Thr Thr Ser Tyr Lys
            180                 185                 190
Leu Thr Ser Cys Asn Thr Ser Val Ile Thr Gln Ala Cys Pro Lys Val
        195                 200                 205
Ser Phe Glu Pro Ile Pro Ile His Tyr Cys Ala Pro Ala Gly Phe Ala
    210                 215                 220
Ile Leu Lys Cys Asn Asn Lys Thr Phe Asn Gly Thr Gly Pro Cys Thr
225                 230                 235                 240
Asn Val Ser Thr Val Gln Cys Thr His Gly Ile Arg Pro Val Val Ser
                245                 250                 255
Thr Gln Leu Leu Leu Asn Gly Ser Leu Ala Glu Glu Glu Val Val Ile
            260                 265                 270
Arg Ser Val Asn Phe Thr Asp Asn Ala Lys Thr Ile Ile Val Gln Leu
        275                 280                 285
Asn Thr Ser Val Glu Ile Asn Cys Thr Arg Pro Asn Asn Asn Thr Arg
    290                 295                 300
Lys Arg Ile Arg Ile Gln Arg Gly Pro Gly Arg Ala Phe Val Thr Ile
305                 310                 315                 320
Gly Lys Ile Gly Asn Met Arg Gln Ala His Cys Asn Ile Ser Arg Ala
                325                 330                 335
Lys Trp Asn Asn Thr Leu Lys Gln Ile Ala Ser Lys Leu Arg Glu Gln

-continued

```
                340                 345                 350
Phe Gly Asn Asn Lys Thr Ile Ile Phe Lys Gln Ser Ser Gly Gly Asp
            355                 360                 365
Pro Glu Ile Val Thr His Ser Phe Asn Cys Gly Gly Glu Phe Phe Tyr
        370                 375                 380
Cys Asn Ser Thr Gln Leu Phe Asn Ser Thr Trp Phe Asn Ser Thr Trp
385                 390                 395                 400
Ser Thr Glu Gly Ser Asn Asn Thr Glu Gly Ser Asp Thr Ile Thr Leu
                405                 410                 415
Pro Cys Arg Ile Lys Gln Ile Ile Asn Met Trp Gln Lys Val Gly Lys
            420                 425                 430
Ala Met Tyr Ala Pro Pro Ile Ser Gly Gln Ile Arg Cys Ser Ser Asn
        435                 440                 445
Ile Thr Gly Leu Leu Leu Thr Arg Asp Gly Gly Asn Ser Asn Asn Glu
    450                 455                 460
Ser Glu Ile Phe Arg Pro Gly Gly Gly Asp Met Arg Asp Asn Trp Arg
465                 470                 475                 480
Ser Glu Leu Tyr Lys Tyr Lys Val Val Lys Ile Glu Pro Leu Gly Val
                485                 490                 495
Ala Pro Thr Lys Ala Lys Arg Arg Val Val Gln Arg Glu Lys Arg Ala
            500                 505                 510
Val Gly Ile Gly Ala Leu Phe Leu Gly Phe Leu Gly Ala Ala Gly Ser
        515                 520                 525
Thr Met Gly Ala Ala Ser Met Thr Leu Thr Val Gln Ala Arg Gln Leu
    530                 535                 540
Leu Ser Gly Ile Val Gln Gln Asn Asn Leu Leu Arg Ala Ile Glu
545                 550                 555                 560
Ala Gln Gln His Leu Leu Gln Leu Thr Val Trp Gly Ile Lys Gln Leu
                565                 570                 575
Gln Ala Arg Ile Leu Ala Val Glu Arg Tyr Leu Lys Asp Gln Gln Leu
            580                 585                 590
Leu Gly Ile Trp Gly Cys Ser Gly Lys Leu Ile Cys Thr Thr Ala Val
        595                 600                 605
Pro Trp Asn Ala Ser Trp Ser Asn Lys Ser Leu Glu Gln Ile Trp Asn
    610                 615                 620
His Thr Thr Trp Met Glu Trp Asp Arg Glu Ile Asn Asn Tyr Thr Ser
625                 630                 635                 640
Leu Ile His Ser Leu Ile Glu Glu Ser Gln Asn Gln Gln Glu Lys Asn
                645                 650                 655
Glu Gln Glu Leu Leu Glu Leu Asp Lys Trp Ala Ser Leu Trp Asn Trp
            660                 665                 670
Phe Asn Ile Thr Asn Trp Leu Trp Tyr Ile Lys Leu Phe Ile Met Ile
        675                 680                 685
Val Gly Gly Leu Val Gly Leu Arg Ile Val Phe Ala Val Leu Ser Ile
    690                 695                 700
Val Asn Arg Val Arg Gln Gly Tyr Ser Pro Leu Ser Phe Gln Thr His
705                 710                 715                 720
Leu Pro Thr Pro Arg Gly Pro Asp Arg Pro Glu Gly Ile Glu Glu Glu
                725                 730                 735
Gly Gly Glu Arg Asp Arg Asp Arg Ser Ile Arg Leu Val Asn Gly Ser
            740                 745                 750
Leu Ala Leu Ile Trp Asp Asp Leu Arg Ser Leu Cys Leu Phe Ser Tyr
        755                 760                 765
```

```
His Arg Leu Arg Asp Leu Leu Leu Ile Val Thr Arg Ile Val Glu Leu
    770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
                805                 810                 815

Ala Thr Ala Ile Ala Val Ala Glu Gly Thr Asp Arg Val Ile Glu Val
                820                 825                 830

Val Gln Gly Ala Cys Arg Ala Ile Arg His Ile Pro Arg Arg Ile Arg
            835                 840                 845

Gln Gly Leu Glu Arg Ile Leu Leu
    850                 855

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Asp Glu Leu
 1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

His Ile Glu Leu
 1

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Phe Pro Lys Asp Glu Leu
 1               5
```

SINGLE CELL ANALYSIS OF HIV REPLICATION CAPACITY AND DRUG RESISTANCE

RELATED APPLICATIONS

This application claims benefit of U.S. Provisional Application 60/540,716 filed Jan. 30, 2004.

This invention was made with Government support under AI-43222 and AI-51178 awarded by the Public Health Service. The Government has certain rights in the invention.

BACKGROUND OF THE INVENTION

1. Field of the Invention

The invention relates generally to the field of medical treatment in relation to assays such as those designed to assist in evaluating drug regimens. The invention also provides novel vectors useful for single cell analysis.

2. Description of the Background Art

Human Immunodeficiency Virus (HIV) is the causative agent for Acquired Immuno-Deficiency Syndrome (AIDS), one of the world's most feared diseases. HIV has been the cause of death for over 15 million people and millions more are infected with the HIV virus. It is estimated that in sub-Saharan Africa there are approximately 28 million people infected with HIV. The AIDS virus is unique in that it is insidious, infecting CD4 cells in the body. These cells are a type of white blood cell the body uses to fight infection, but after infection the CD4 cells produce virus, not more CD4 cells.

Once the CD4+ cell count has been reduced to less than 200, the immune defense has become seriously compromised, leaving the body vulnerable to opportunistic infections such as pneumonia, tuberculosis and some forms of cancer. In fact the cause of death in AIDS patients is usually from an infection and not directly from HIV.

There is no known cure for AIDS, nor has a protective vaccine been developed. There are medications that will slow viral replication and in many cases enable HIV-positive patients to live a near normal life. Treatments are expensive and have included use of antiretrovirals such as reverse transcriptase (RT) protease inhibitors (PIs). Current treatment of choice is use of combinations of drugs, each of which acts somewhat differently, with close monitoring of patient health so that dosages and combinations can be adjusted.

HAART

HIV treatment has evolved considerably since the first retroviral inhibitors were used. Current therapies employ a panel of therapeutics, known as Highly Active Anti-Retroviral Therapy (HAART). HAART is an aggressive therapy utilizing a multiple of anti-HIV drugs, not only for patients with AIDS but also to some HIV-positive subjects even before they develop symptoms of AIDS. The therapy commonly includes one nucleoside analog (such as a DNA chain terminator), one protease inhibitor and either a second nucleoside analog or a non-nucleoside reverse transcription inhibitor (NNRTI).

There are a number of drugs used in HAART therapy, of which azidothymidine (AZT) is one of the earliest and best-known nucleoside analogs used in treating AIDS. Other drugs used in combinational HAART therapies include zalcitabine (ddC), didanosine (ddI), amprenavir (AVP), Ritonavir (RTV), abacavir (ABC), tenofovir disoproxil fumarate, (TDF), nelfinavir (NFV), saquinavir (SQV), lopinavir (LPV) and indinavir (IDV)

Unfortunately, HAART is a difficult treatment because of toxicity, treatment failure or side effects Baron, et al. (2004). Adherence to prescribed regimens is not always easy to determine and patient compliance is often low, which may be due in part because there are no established standards for assessing compliance. The toxicity and tolerability of HAART are increasingly important factors in decisions relating to considering which of more than 6000 potential regimen combinations to prescribe or, perhaps more importantly, when to modify or discontinue a particular regimen.

Adverse effects are associated with each class of drug used in HAART. Nucleoside analogs have been reported to cause severe nucleoside associated lactic acidosis (NALA), or pancreatitis. The protease drugs are associated with hypertriglyceridemia, insulin resistance, diarrhea, nausea, headache and oral paresthesia. IL-2 combination therapies have been associated with fever, fatigue and myalgias.

Auxiliary therapy is often required in AIDS treatment because patients with compromised immune systems are susceptible to many types of infections, particularly *pneumocystis carinii* pneumonia (PCP) and tuberculosis. Adverse effects to drugs used in treatment of these conditions complicates AIDS therapy and may contribute to death of a patient.

Resistance to AIDS therapy is one of the most compelling problems in managing drug regimens. HIV RNA levels are the usual means of monitoring viral load and progress of the therapy.

Perhaps the most challenging aspect of the HIV is its ability to rapidly mutate in infected patients. In the United States at least, the infecting virus "wildtype" is HIV-1, although in some other parts of the world HIV-2 is more common. The number of naturally occurring mutations is high and many of the amino acid changes known to contribute to drug resistance occur as natural polymporphisms in isolates from patients who have never been treated with protease inhibitors (Kozal, et al. (1996). A great deal is known about the mutations that confer resistance to antiretroviral drugs, although development of drugs to effectively combat the mutant virus is relatively slow compared to the pace at which HIV mutations can appear.

Several assays have been used to monitor the development of drug resistance. Population-level sequencing of viruses in plasma can reveal the existence of characteristic mutations associated with drug resistance. Genotypic data can be used to predict drug resistance phenotypes by using compiled databases and established algorithms.

Direct phenotypic assays of drug resistance have also been developed (Petropoulos, et al, 2000) and are of particular value when multiple mutations are present. These assays use pooled HIV-1 reverse transcriptase (RT) and protease sequences amplified from plasma to measure susceptibility to individual antiretroviral drugs. The interpretation of these assays is complicated by the fact that viruses replicating in vivo experience simultaneous selection by each of the drugs in the regimen. The possible synergy and antagonism that may occur with treatment with multiple agents are not reflected in current assays. A particular problem is that current assays do not provide a clear indication of whether or not multiple antiretroviral drugs acting synergistically might still have some residual activity against viruses with resistance mutations. Thus, phenotypic assays that can compare the susceptibility of viral isolates to drug combinations, rather than to individual drugs, would be a valuable tool for choosing alternative regimens in the setting of treatment failure.

The choice of treatment regimens in the setting of failure is further complicated by the issue of replication capacity. Studies by Deeks et al. (2001) have demonstrated that some patients who are failing therapy maintain relatively high CD4 counts despite detectable viremia. Interruption of therapy leads to the loss of this immunologic benefit. Because some drug resistance mutations can reduce the fitness of the virus relative to wild-type virus in the absence of drugs (Nijhuis, et al. 2001), some investigators suggested that the immunologic benefit of continued treatment in the presence of virologic failure may reflect selection for drug-resistant mutants with diminished replication capacities (Barbour, et al., 2002). This benefit is entirely dependent upon the assumption that the wild-type virus with higher fitness is preserved and will reappear if therapy is stopped. Indeed, wild-type viruses do reappear several weeks after treatment interruption (Deeks, et al., 2001).

The reappearance of wild-type virus is unlikely to be simply genetic reversion because different forms of resistance involving either single mutations or accumulations of multiple mutations disappear with similar kinetics. Phylogenetic evidence suggests that the reemerging wild-type viruses are archival (Kijak, et al., 2002). At the present time, the only site in which wild-type viruses have been shown to persist despite prolonged replication of and selection for drug-resistant viruses is the latent reservoir in resting memory CD4+ T cells.

Deficiencies in the Art

A major concern in treating HIV patients receiving HAART is the ability of the virus to mutate, often resulting in less effective treatment or treatment failure. There is a need for methods that provide guidelines for determining whether or not to continue or adjust drug regimens for HIV patients. Patients failing HAART may nevertheless derive benefit from continued treatment for two reasons, namely the residual susceptibility of the resistant viruses to the drug regimen and the diminished replication capacities of the resistant viruses. Current assays do not provide a simple way to determine the relative importance of these two effects, making it difficult for the clinician to determine any potential benefit from continued therapy or rationally adjusted therapy with respect to the number and type of antiviral drugs administered.

SUMMARY OF THE INVENTION

The invention addresses one of the more frustrating problems in clinical treatment of AIDS patients, which frequently arise because use of HAART, currently a widely used therapy, becomes less effective in controlling viral load and maintenance of near normal CD4+ cell levels. In particular, a novel method of determining the replicative capacity of drug-resistant HIV in HAART-treated patients has been developed. Using a series of in vitro measurements of drug resistance of mutant virus from the patient, compared with resistance of the wildtype virus originally treated, a clinical test has been designed. The measurements obtained from the disclosed assay will permit the physician to make rational decisions relating to continuing, adjusting or discontinuing multiple drug regimens.

An important and novel feature of the invention is the design of HIV vectors that are capable of infecting a competent host cell; i.e. a viral replicating cells, and which deliver a detectable protein to the endoplasmic reticulum (ER) of the host cell. The protein is a tagged fluorescent protein such as green fluorescent protein (GFP), red fluorescent protein (DsRed) and the like, which after viral replication remains associated with the ER of the host cell because of a fused signaling sequence. A preferred fluorescent protein is green fluorescent protein, but other fluorescent proteins are available; for example, red fluorescent proteins such as DsRed (available in a color series from Clontech, Palo Alto, CA), reef coral fluorescent proteins available with emission manima in ranges 489-539 nm and several color modifications of green fluorescent protein with emission maxima ranges from 476-529 nm. The ER targeting feature is due to fusion of a short C-terminal signal protein such as KDEL (SEQ ID NO: 14) or HIEL (SEQ ID NO: 15) to the fluorescent protein.

The targeting and subsequent association of the fluorescent protein to the host cell ER is accomplished by engineering a fluorescent protein incorporating a signal sequence, which is expressed as a fusion polypeptide in the host cell and remains anchored in the ER of the host cell, while not affecting the normal expression of the HIV. This allows an accurate count of the number of infected cells, in turn allowing a determination of replicative capacity of drug-resistant mutant virus in the patient.

An exemplary signal sequence is KDEL (SEQ ID NO: 14), as illustrated in the model construct described herein; however similar targeting sequences known in the art may be employed; for example, HIEL (SEQ ID NO: 15). It is important that the expressed fusion protein remain in the host cell ER; otherwise, an accurate measurement of HIV-replicative capacity cannot be determined.

The HIV vector is designed so that the fluorescent protein inserts into the HIV genome at a deletion position in the env polynucleotide sequence. The insertion contains the coding signal for the tag protein in frame with the ER targeting polypeptide so that a targeting polypeptide tag, preferably a fluorescent protein, is expressed. While the designed HIV vector preferably incorporates a fluorescent protein, other detectable tags are envisioned, such that the constructs may be engineered with radiolabels or colorimetric labels, so long as single cell separation/detection means are employed.

The invention thus in one aspect is a single-cell-level phenotypic assay that allows analytical comparison of the contributions of residual susceptibility and reduced replication capacity, thereby addressing the need to provide a rational basis for treatment decisions in the setting of virologic failure.

As discussed, a novel HIV vector designed to express a fluorescent protein in the endoplasmic reticulum of an infected cell forms the basis of the new phenotypic assay. The env region of HIV is modified by deleting a region beginning about 125 bp or so downstream from the N-terminus and inserting a coding sequence for a fluorescent protein fused with a signal sequence that causes the expressed fluorescent protein to be retained in the endoplasmic reticulum of an infected cell.

An exemplary fusion sequence is GFP in frame with KDEL (SEQ ID NO: 14) and a stop codon. The fusion protein coding sequence is preferably inserted near the N-terminus of the env gene, about 125 bp downstream, or in such a position that the N-terminus signal region responsible for importing the protein into the endoplasmic reticulum of the infected cell is retained. While exemplified with GFP, other fluorescent proteins may be used and engineered in frame with a stop codon, exemplified with TAA. It is believed that there are several suitable deletions that could be used in place of deleted 6351-7260. Variations of the vector are possible, all of which can be readily constructed by those of skill in the art.

In an exemplary HIV vector embodiment, a GFPKDEL (SEQ ID NO: 16) fusion protein in frame with TAA is inserted within deleted positions 6351 to 7260 of the HIV-1 env gene. The gag-pol sequence may be wildtype or heterologous; that is, gag-pol obtained HIV-1 or from a variant or mutant HIV. Mutant HIV-1 is typically detected in human patients undergoing retroviral drug treatment. While the originally infecting "wildtype" HIV-1 may be present, the mutant(s) begin to predominate and exhibit increased resistance to drug therapies.

In an exemplary HIV vector embodiment, a GFPKDEL fusion protein in frame with TAA is inserted within deleted positions 6351 to 7260 of the HIV-1 env gene. The gag-pol sequence may be wildtype or heterologous; that is, gag-pol obtained HIV-1 or from a variant or mutant HIV. Mutant HIV-1 is typically detected in human patients undergoing retroviral drug treatment. While the originally infecting "wildtype" HIV-1 may be present, the mutant(s) begin to predominate and exhibit increased resistance to drug therapies.

Recombinant HIV-1 vectors containing patient-derived gag-pol sequences are prepared by replacing the 1.5 ApaI/ AgeI fragment of pNF4-3-DE-GFP (see FIG. 8) with the patient-derived gag-pol sequences. Of course other deletion/ insertion modifications could be used, so long as replicative capacity is not significantly altered compared with in vivo replicative capacity.

A particularly important source of heterologous gag-pol sequences are from HIV samples from human patients who are undergoing highly active anti-retroviral therapy (HAART) and who show indications of development of drug resistance. The resistance usually develops because of virus mutation; however, because HAART utilizes a combination of several drugs, often three or four, it is often not immediately clear which of the drugs has become ineffective. There are only about 20 drugs currently used to formulate the most appropriate mixtures, yet the drug combinations are several thousand. Some of the more commonly used drugs for HAART combinations are zalcitabine (ddC), didanosine (ddI) amprenavir (AVP), Ritonavir (RTV), abacavir (ABC), tenofovir disoproxil fumarate (TDF), nelfinavir (NFV), saquinavir (SQV), lopinavir (LPV) and indinavir (IDV).

Yet another aspect of the invention includes HIV pseudotypes. These are particularly useful for in vitro assays to measure viral replication or, as used herein, viral replicative capacity. Pseudotyped viruses are well known and generally are the replacement of part of a viral coat protein with a heterologous protein. In an exemplary embodiment, vesicular stomatitis virus glycoprotein (VSV-G) was pseudotyped with HIV-1, by transfecting competent cells with pVSV-G and wt or recombinant pNL4-3-DE-GFP (described above). Other pseudotypes could be employed; for example, heterologous HIV env protein.

The present invention takes advantage of pseudotyped HIV to prepare pseudotyped HIV stocks from patient HIV. This is accomplished by coinfecting or cotransfecting VSV-G and the disclosed HIV vector into a cell and preparing pseudotyped stocks of HIV. The stocks can be "normalized" by measuring the number of cells in an aliquot expressing a detectable protein, such as fluorescent protein GFP.

A particularly novel aspect of the invention is the use of normalized pseudotyped HIV stocks to determine HIV replicative capacity of the virus from AIDS patient samples. The method includes the steps of transfecting a selected host cell with the described pseudotyped HIV, culturing the transfected cell to obtain a stock of pseudotyped HIV; normalizing said stock by determining the number of transfected cells expressing fluorescent protein in an aliquot of the stock; and infecting a population of target cells with an amount of stock supernatant containing a determined number of transfected cells. This provides the number of infected target cells is indicative of HIV replication capacity. The number of infected target cells will fluoresce when GFP or other fluorescent protein is encoded in the HIV env and can be quantified by methods such as flow cytometry.

The target cell is preferably a T-cell and most preferably a CD4+ cell because those are the cells infected by HIV. Host cells can be selected from a range of suitable cells that are capable of supporting HIV replication, including Jurkat cells, 293T cells and CD4+ cells.

In medical practice, the novel assay can be used to assess drug susceptibility of HIV-1 infected patients. The method involves the steps of first preparing a normalized HIV pseudovirus stock as described where the gag-pol is from an HIV-1 infected patient. A second normalized HIV pseudovirus stock is also prepared where the gag-pol is from wildtype HIV. Preferably, the wildtype HIV will be the same HIV that infected the patient when originally treated. The next step is to infect different selected target virus-producing cell samples in vitro, one with an aliquot of the first normalized pseudovirus stock and the other with the second normalized pseudovirus stock. The pseudovirus in each sample is then replicated. The whole process is repeated with each for the infection steps, except that infection is conducted in the presence of the drugs being used to treat the patient. The relative differences between replication capacity of the patient's (mutant) pseudovirus and the wildtype virus are compared. This comparison is a measure of drug susceptibility of the HIV-1 infected patient.

Susceptibility measure can be used to evaluate selection of a drug regimen for AIDS patients resistant to HAART therapy. Drug susceptibility of the AIDS patient is determined as described by calculating the replicative capacity ratio of patient mutant HIV/patient wildtype HIV, the repeating the measure and ratio determination in the presence of drugs employed in the HAART. The two ratios are compared and used to provide an indication of whether or not to continue current HAART, modify HAART or discontinue altogether the particular drugs used. The ratio of the two ratios is a "replication capacity index" (RCI) and has been assessed for several HAART regimens (see Table 2). Where the RCI is less than 1, and the wildtype is strongly inhibited by the drug regimen while the drug-resistant isolate only partially inhibited, there is indication that HAART may control viremia, suggesting continuation of HAART.

Where the RCI is greater than 1 relative to wildtype and drug resistant HIV-1 has a high replication capacity and minimal drug susceptibility, the resistant isolate is highly fit despite its mutations and was only minimally suppressed by HAART. Such comparisons indicate that at least for the isolate examined, HAART is of little use.

In another instance, the RCI is greater than or almost equal to 1 at both minimal and maximal drug concentrations indicating resistance, yet the replication capacity compared to wildtype was diminished. This suggests that if a patient has a wildtype virus similar to the standard wildtype incorporated in pNL4-3, HAART may still benefit by selecting for a resistant variant with reduced replication capacity.

BRIEF DESCRIPTION OF THE FIGURES

(FIG. 1A) Proviral construct used to generate pseudotyped virus for infections. Patient-derived gag-pol sequences were cloned in frame into a pNL4-3 proviral clone with the coding sequence for GFP replacing a portion of the env gene. The GFP sequence was followed by a KDEL (SEQ ID NO: 14) ER retention signal and a stop codon. As a result, cells transfected with this vector or infected with pseudotyped viruses generated from this vector express an Env-GFP fusion protein that is directed into the ER by the Env signal peptide and retained in the ER by the KDEL (SEQ ID NO: 14) sequence. (FIG. 1B) Expression of GFP by infected CD4+T cells. The CD4+-T-cell Jurkat line was infected in vitro with GFP-encoding HIV-1 pseudotyped with VSV-G. Representative dot plots of GFP expression are shown for uninfected Jurkat cells (left), Jurkat cells infected with pseudovirions carrying the reference NL4-3 gag-pol sequence (center), and Jurkat cells infected with pseudovirions carrying a patient-derived wild-type gag-pol sequence, Pt0311-5M7 (right). (FIG. 1C) Linear relationship between the number of infected Jurkat cells and the amount of input viral inoculum. Jurkat cells were infected under standard conditions with increasing amounts of viral supernatant equivalent to the indicated numbers of virus-producing cells. GFP expression in Jurkat cells was measured by flow cytometry on day 2 after infection. The dotted line represents a fitted linear regression.

FIG. 5A. Resistant virus with significant residual susceptibility and marginally reduced replication capacity. FIG. 5B. Resistant virus with minimal residual susceptibility and high replication capacity. FIG. 5C. Resistant virus with no residual susceptibility and significantly reduced replication capacity.

DETAILED DESCRIPTION OF THE INVENTION

Figure 1:
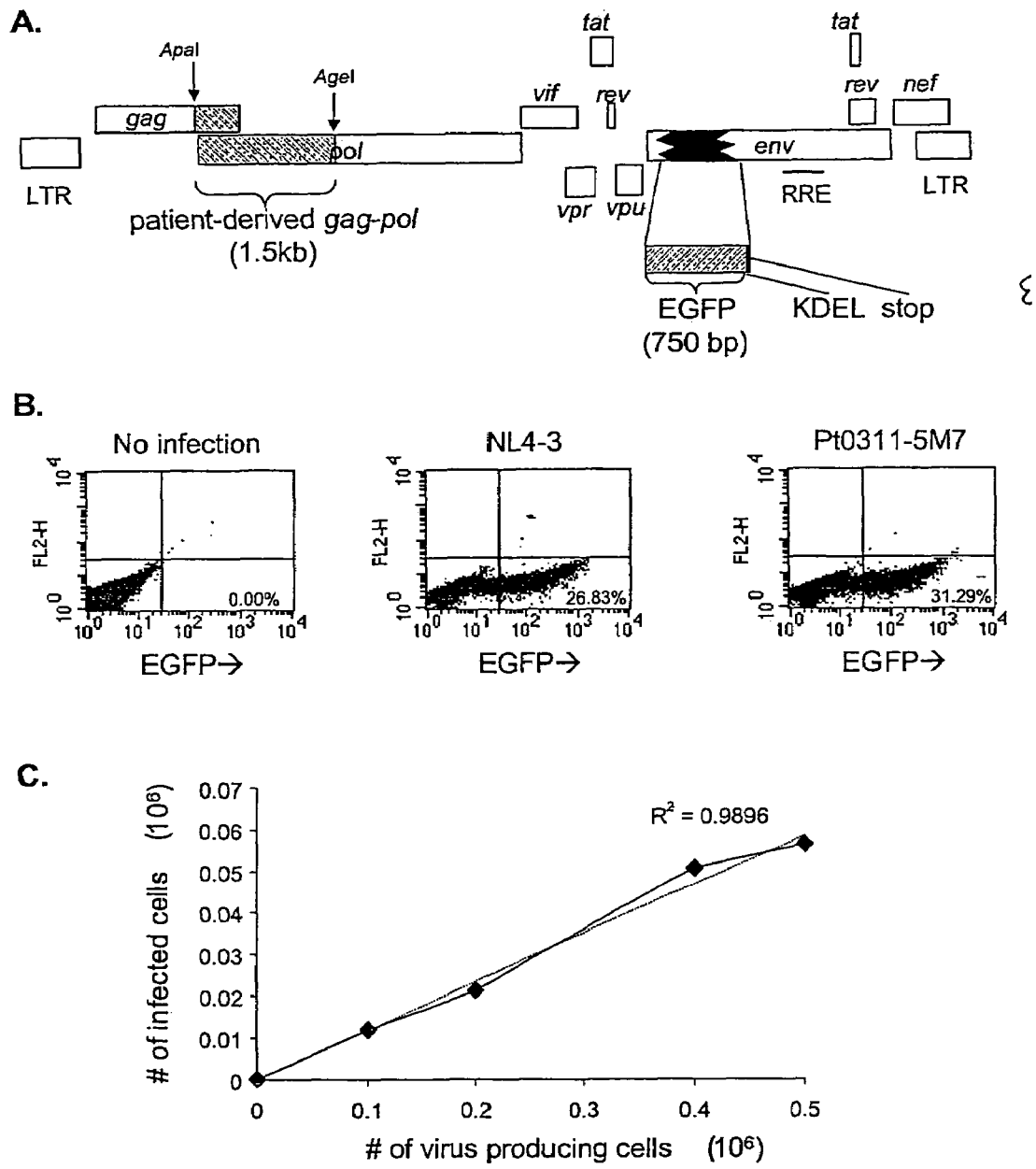
FIG. 1. Single-cell phenotypic assay for drug susceptibility and replication capacity.

The following terms used herein are clarified and defined as follows:

"Archival" refers to viruses that have replicated previously in the patient and then stored in a latent form in resting CD4+ cells.

"Fit" refers to a virus that is capable of replicating efficiently.

"Replicative capacity" refers to the fitness of a virus in the absence of any drug pressure.

The invention provides a novel phenotypic assay that can simultaneously measure, on the same scale, HIV-1 susceptibility to drug combinations and changes in replication capacity relative to reference or patient-specific wild-type sequences. This provides a quantitative tool for analyzing the efficacy of antiretroviral therapy, especially the mechanism of the clinical benefit of HAART in the setting of virologic failure.

While no in vitro assay can fully duplicate the in vivo conditions under which the antiretroviral drugs mediate suppression of viral replication; nevertheless, in vitro phenotypic assays of drug resistance have potential clinical utility (Katzenstein, et al., 2003; Shulman, et al., 2002). Results from single-cycle assays of replication capacity generally parallel results of virus culture assays for fitness (Resch, et al., 2002), although the correlation is not always perfect.

In the assay described here, several steps have been taken to ensure that the cultures mimic in vivo conditions as closely as possible. First, the protein binding properties of some antiretroviral drugs have been accounted for by supplementing the culture medium with 50% normal human serum.

Second, the prodrug activation required for the function of all NRTIs has also been taken into account. Because all NRTIs require multiple steps of intracellular phosphorylation to be converted to active nucleoside triphosphate analogues, CD4+ T cells were pretreated with NRTIs 16 h prior to infection. This time is sufficient for intracellular levels of the active forms of these drugs to reach a steady state, as evidenced by the fact that pretreatment for longer times does not increase inhibition.

Third, drugs were tested at their Cmin and Cmax values under the conditions described above. This effectively circumvents issues related to drug absorption and metabolism and exposes target cells to concentrations of drugs that bracket the concentrations that should be experienced by cells in vivo.

Finally, and most significantly, the drugs were tested in the same combinations that are used in vivo. Because many combinations of antiretroviral drugs produce a profound synergistic inhibition of wild-type virus, quantitative analysis of drug inhibition is only possible with assays that have a wide dynamic range. The flow cytometric assay described here has a dynamic range of up to 4 logs, allowing quantification of the synergistic inhibitory effects of drug combinations as well as of individual components of the regimen. The assay faithfully reproduced reported drug interactions that occur at the level of target cells. For example, the reported antagonism between AZT and d4T caused by competition at the step of prodrug activation was readily observed with this assay (Table 1). Taken together, these results suggest that the disclosed phenotypic assay provides a reasonable first approximation of drug inhibitory effects in vivo.

Using this assay, the potencies of available antiretroviral drugs were compared by examining the ratio of the $C_{min}$ and Cmax values to the $IC_{50}$ determined in this system. The data highlight the extraordinary potency of the NNRTI EFV, which has a Cmin/$IC_{50}$ ratio of >1,000 in the disclosed system. In contrast, the commonly used NRTIs d4T and ddI are relatively inefficient at inhibiting viral replication in this system. $C_{max}$ values for these drugs are actually below the $IC_{50}$ and $IC_{90}$ values, respectively. Because the actual $IC_{50}$ depends on the viral strain, the target cell type, the culture medium, and the multiplicity of infection in specific phenotypic assay systems, direct comparison of Cmin $IC_{50}$ and Cmax/$IC_{50}$ ratios between different assay systems is not possible.

Drug susceptibility measured in the disclosed system was also dependent on the properties of the virus-producing cells, 293T cells, and the target cells, the Jurkat CD4$^+$-T-cell line. These cells may differ from primary CD4$^+$ T cells in the absorption and metabolism of antiretroviral drugs. They may differ from primary cells in the expression of transporters, such as the P glycoprotein, that can export PIs from the cytoplasm. The in vivo efficacy of a drug is dependent upon more than its potency in inhibiting a single round of viral replication. Additional factors such as genetic barriers to resistance, tolerability, and pharmacokinetics may have an effect and these also contribute to contribute to inaccuracy in methods that utilize a single round of replication as basis for measurement.

The heterogeneity of replication capacities of wild-type HIV-1 isolates relative to that of a reference sequence, NL4-3, will have some effect on the accuracy of the results. The replication capacities of wildtype HIV-1 clones from patients vary up to 2.5-fold from NL4-3 capacity measured in the disclosed system. Mean replication capacity index relative to NL4-3 was 0.81±0.34 (n=7) in the examples reported herein. These results indicate that in order to most accurately assess changes in viral fitness in vivo, it is necessary to compare the replication capacity of the patient's drug-resistant virus to that of the drug-sensitive virus obtained from the same patient. This is readily done in the system described here, provided that the wild-type sequence is available.

In compliant patients who are failing therapy and have drug-resistant viruses, wild-type viruses are typically not found in the plasma but do persist in the latent reservoir in resting memory CD4$^+$ T cells. Viral clones with different mutations are likely to be present in each patient with drug resistance and so that results of this type of analysis may be different for each clone. Ideally, a large number of distinct clones representing the full range of variation in pol should be analyzed, although this may not be practical as a routine clinical test. Alternatively, analysis of selected clones that represent extremes on the spectrum of wild-type to fully resistant viruses should provide meaningful data. Another factor affecting viral fitness are the compensatory mutations outside of the gag-pol region; however, the construct employed in the present invention includes the Gag p7/p1 and p1/p6 cleavage sites that frequently accumulate compensatory mutations in response to PIs.

Figure 7:
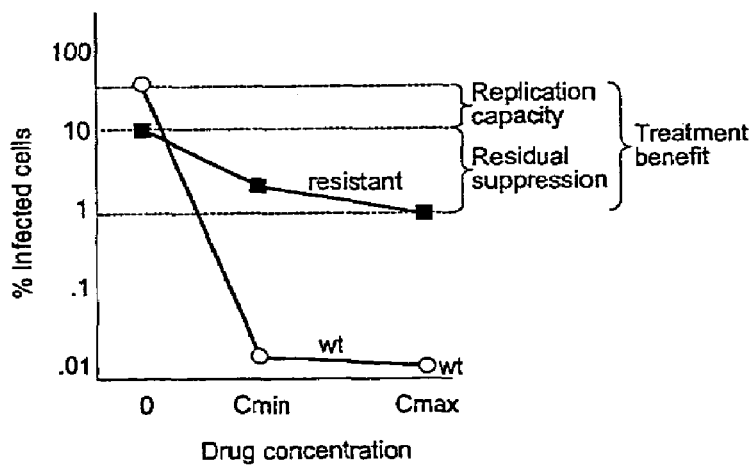
FIG. 7. Schematic plot showing decomposition of the clinical benefit of nonsuppressive HAART into two additive effects, the residual suppression of viral replication and the selection for resistant virus with diminished replication capacity. The difference in viral replication in the absence of drug represents the diminished replication capacity of the selected resistant virus versus the counterselected archival wildtype virus. The different replication capacities of the resistant virus in the absence and presence of the failing drug regimen represent residual suppression of the resistant virus. The addition of these two effects on a log scale represents the total inhibition of potential viral replication by nonsuppressive HAART or the treatment benefit.
Figure 8:
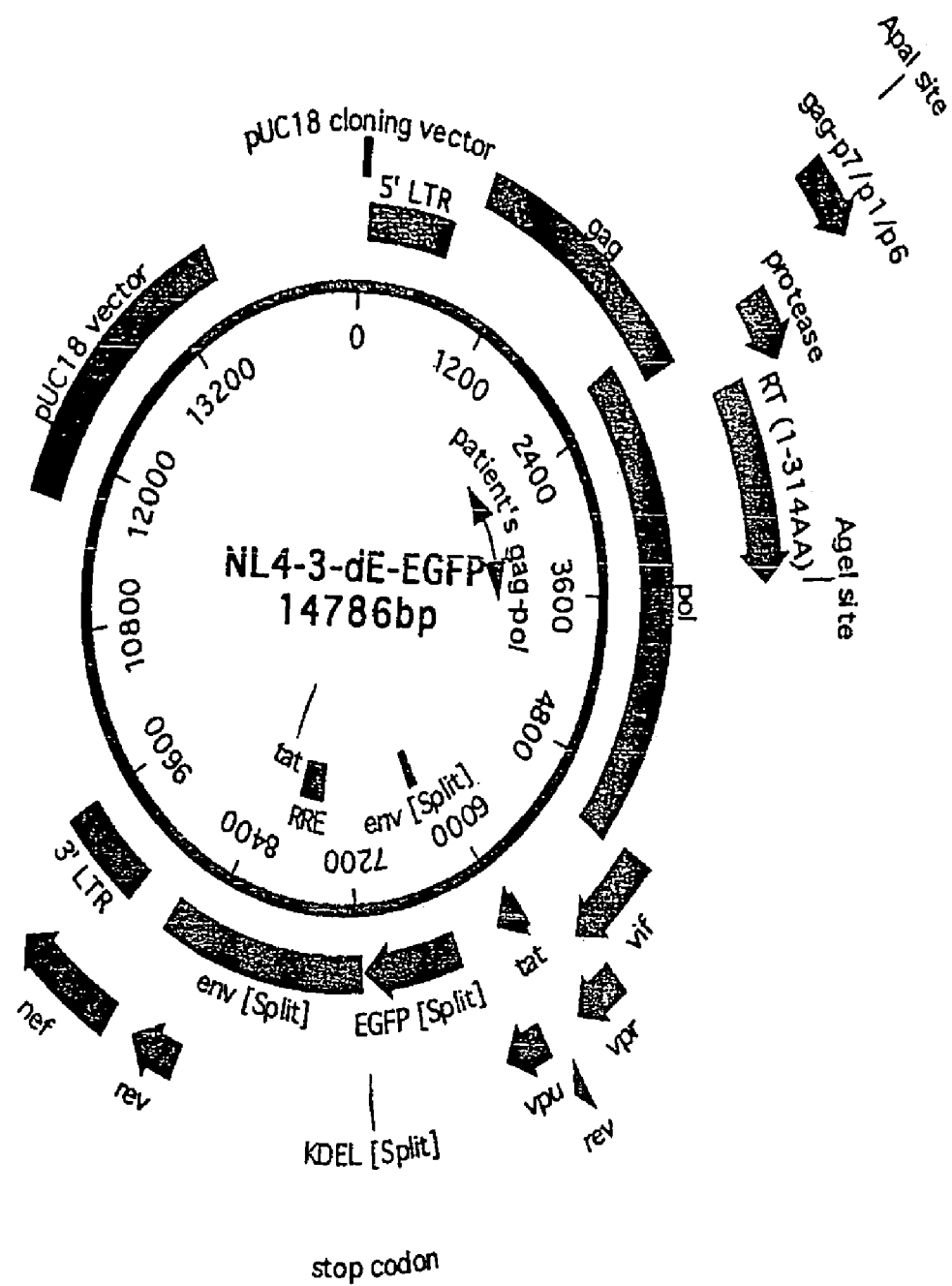
FIG. 8. pUC 18 cloning vector showing the engineered construct for pNL4-3-dE-EGFP. KDEL disclosed as SEQ ID NO: 14

The ability of the novel assay to simultaneously measure HIV-1 drug susceptibility and replication capacity permits an assessment of the mechanisms of the apparent clinical benefit of HAART in the setting of virologic failure. The data presented here show that the benefit of nonsuppressive HAART can be quantitatively deconstructed into two additive effects. This is illustrated graphically in FIG. 7 and numerically in Table 2. One effect is the residual suppression of replication of the resistant variants by antiretroviral drugs. This is a benefit that operates in real time, reflecting direct inhibition of viral enzymes by the drugs.

An additional beneficial feature of the invention is the assessment of whether or not the drug regimen will allow selection for drug-resistant variants with a diminished replication capacity. The importance of selection for such variants becomes apparent if the drugs are stopped and archived drug-sensitive variants with higher replication capacities emerge. A recent study by Ruff et al. (2002) demonstrated the persistence of archival wild-type HIV-1 in the latent reservoir in resting memory CD4$^+$ T cells even after years of selection for drug-resistant variants by failing drug regimens. Further evidence for the persistence of wild-type viruses in the setting of failure comes from the work of Deeks et al. (14) demonstrating simultaneous loss of all drug-resistant variants accompanied with the appearance of wild-type HIV-1 in patients with multidrug resistance who interrupt therapy. These data suggest that the selection pressure exerted by drugs in failing regimens can prevent drug-sensitive variants with potentially higher replication capacities from emerging.

The analysis of HAART therapy and the assay method for residual drug susceptibility and reduced replication capacity of drug resistant HIV-1 provides the basis for the rational management of antiretroviral therapy in the problematic setting of virologic failure. For example, in circumstances in which the clinical benefit of the drug combination is solely due to selection for resistant variants with diminished replication capacities, as shown in FIG. 5C, the drug regimen can be simplified, retaining the minimum number of drugs needed to provide selection pressure favoring the resistant variants over the wild-type virus. On the other hand, in cases in which the HAART regimen exerts little suppression on viral replication and the evolved resistant virus has achieved a replication capacity equivalent to that of the archived wild-type viruses present in the latent reservoir (FIG. 5B), continued treatment with the same regimen provides no obvious benefit.

Human immunodeficiency virus type 1 (HIV-1)-infected individuals who develop drug-resistant virus during antiretroviral therapy may derive benefit from continued treatment for two reasons. First, drug-resistant viruses can retain partial susceptibility to the drug combination. Second, therapy selects for drug-resistant viruses that may have reduced replication capacities relative to archived, drug-sensitive viruses.

The present invention is a novel single-cell-level phenotypic assay that allows these two effects to be distinguished and compared quantitatively. Patient-derived gag-pol sequences were cloned into an HIV-1 reporter virus that expresses an endoplasmic reticulum-retained Env-green fluorescent protein fusion. Flow cytometric analysis of single-round infections allowed a quantitative analysis of viral replication over a 4-log dynamic range. The assay faithfully reproduced known in vivo drug interactions occurring at the level of target cells. Simultaneous analysis of single-round infections by wild-type and resistant viruses in the presence and absence of the relevant drug combination divided the benefit of continued nonsuppressive treatment into two additive components, residual virus susceptibility to the drug combination and selection for drug-resistant variants with diminished replication capacities.

In some patients with drug resistance, the dominant circulating viruses retained significant susceptibility to the combination. However, in other cases, the dominant drug-resistant viruses showed no residual susceptibility to the combination but had a reduced replication capacity relative to the wild-type virus. Thus, simplification of the regimen may still allow adequate suppression of the wild-type virus. In a third pattern, the resistant viruses had no residual susceptibility to the relevant drug regimen but nevertheless had a replication capacity equivalent to that of wild-type virus. In such cases, there is no benefit to continued treatment.

The ability to simultaneously analyze residual susceptibility and reduced replication capacity of drug-resistant viruses may provide a basis for rational therapeutic decisions in the setting of treatment failure.

Treatment of human immunodeficiency virus type 1 (HIV 1)-infected patients with highly active antiretroviral therapy (HAART) can reduce plasma virus levels to below the detection limit (Perelson, et al., 1997) and can allow a significant degree of immune reconstitution when control of viremia is maintained (Lederman, et al., 2000). However, eradication of HIV-1 infection has not been achieved despite suppression of viremia to below detection limits for as long as 7 years (Siliciano, et al., 2003). A viral reservoir in latently infected resting memory CD4$^+$ T cells has shown remarkable stability and can support life-long persistence of replication competent HIV-1 (for a review, see Blankson, et al., 2002). This reservoir in resting CD4$^+$ T cells can serve as a permanent archive for all major forms of the virus present during the entire course of infection, including the original drug-sensitive forms as well as drug-resistant viruses that arise due to inadequate suppression of viral replication by antiretroviral drugs (Ruff, et al., 2002).

Although HAART can effectively suppress viremia to below the limit of detection for prolonged periods in some infected individuals, virologic failure, as evidenced by consistently detectable viremia, is also common (Lucas, et al., 1999). Failure is frequently associated with the development of resistance to one or more of the drugs in the regimen, and drug resistance has emerged as a major problem in the management of HIV-1 infection.

The following examples are set forth to assist in understanding the invention and should not be construed as specifically limiting the invention described and claimed herein. Such variations of the invention, including substitution of all equivalents now known or later developed, which would be within the purview of those skilled in the art, and changes in composition and modifications of the procedures and methods are to be considered to fall within the scope of the invention disclosed herein.

EXAMPLES

The following examples, preparation and use of materials are provided to illustrate how to make and use the invention as well as to understand the background in developing the invention. Such examples are in no way to be considered limiting.

Materials and Methods

Vectors. The green fluorescent protein (GFP)-tagged HIV-1 vector pNL4-3-DE-GFP was modified from a previously described reporter virus construct (Pierson, et al., 2002). The KpnI-NheI fragment of the HIV-1 NL4-3 env gene (nucleotides 6351 to 7260 in HXB2 coordinates) was replaced with a 745-bp fragment containing the GFP gene. The deleted env region was downstream of the N-terminal Env signal peptide coding sequence and did not overlap with other HIV-1 open reading frames or the Rev-response element (RRE). The GFP-encoding fragment was amplified from the pEGFP-N1 plasmid (Clontech) with primers containing KpnI and NheI sites (GFP 5'primer, ATTGGGTAC-CTGTCGCCACCATGGTGAGC (SEQ ID NO: 1); GFP 3'primer, GTCCGTGCTAGCTTACAGCTCGTCCTTG-TACAGCTCGTCCATGCC (SEQ ID NO: 2).

The 3' primer introduced an in-frame endoplasmic reticulum (ER) retention signal (KDEL) followed by a TAA stop codon at the end of the GFP gene. To insert the KpnI/NheI-flanked GFP fragment into the pNL4-3 backbone, a three-way ligation was set up, involving the KpnI/NheI-digested GFP PCR product, the 13.3-kb EcoRI/NheI fragment, and the 605-bp EcoRI/KpnI fragment of pNL4-3. Correct construction was verified by MfeI digestion and expression of GFP in transfected 293T cells, as detected by flow cytometry. The GFP-KDEL-stop sequence (KDEL disclosed as SEQ ID NO: 14) was inserted so as to preserve splice junctions as well as the RRE.

Patient samples. gag-pol sequences with drug resistance mutations were obtained from the latent reservoir or plasma of compliant pediatric and adult patients who were failing HAART with consistently detectable viremia. Isolates from the latent reservoir were obtained from replication-competent viruses grown out of the reservoir at a limiting dilution in cultures in which resting cells from patients were stimulated in vitro with mitogens and then cocultured in the presence of CD4$^+$ lymphoblasts from healthy donors (Finzi, et al., 1997).

Insertion of patient-derived HIV-1 gag-pol sequences into pNL4-3-DE-GFP. Recombinant HIV-1 vectors containing patient-derived gag-pol sequences were made by replacing the 1.5-kb ApaI/AgeI fragment of pNL4-3-DE-GFP with corresponding patient-derived sequences amplified by RT-PCR from plasma virus (24) or by PCR from proviral DNA in latently infected resting CD4$^+$ T cells. This portion of the gag-pol gene includes a sequence encoding the Gag protein p7 C terminus, p1 and p6 (Gag codons 406 to 500), full-length protease, and the first 314 amino acids of RT. Viral RNA and proviral DNA were obtained as previously described (Hermankova, et al., 2001). The following nested sets of primers were used for PCR amplification: 5'outer, GCAA-GAGTTTTGGCTGAAGCAATGAG (SEQ ID NO: 3) (HXB2 positions 1867 to 1892); 3'-outer, CCTTGCCCCT-GCTTCTGTATTTCTGC (SEQ ID NO:4) (HXB2 positions 3528 to 3553); 5'-inner, TGCAGGGCCCCTAG-GAAAAAGGGCTG (SEQ ID NO:5) (HXB2 positions 2002 to 2027); 3'-nner, CATGTACCGGTTCTTTTA-GAATCTCTCTGTT (SEQ ID NO:6) (HXB2 positions 3465 to 3495).

ApaI and AgeI sites were incorporated in the 5' and 3' inner primers. PCR was performed with high-fidelity Platinum Pfx DNA polymerase (Invitrogen). The thermocycling protocol was denaturing at 94 C for 3 min, 30 rounds of denaturing-annealing-extension cycles (94° C. for 20 s, 60° C. for 30 s, and 68° C. for 1.5 min), and a final extension at 68° C. for 5 min. The outer PCR products were diluted 1:200 and used as templates in the second-round inner PCR. The 1.5-kb final PCR products were resolved in a 0.7% agarose gel and purified by use of a Qiaquick PCR purification kit (Qiagen). The patient-derived gag-pol PCR products were then cloned into pNL4-3-DE-GFP by ligation of ApaI/AgeI-digested PCR products with the 13.2-kb ApaI/AgeI fragment of pNL4-3-DE-GFP at an insert/vector molar ratio of 5:1. Ligation products were then transformed into STBL-2 competent cells (Invitrogen). Transformants were plated on Luria-Bertani agarose selection medium containing 50 μg of carbenicillin (Sigma)/ml. Positive clones were identified by MfeI digestion and were sequenced by using the following primers: PR, CAGAAAGGCAATTTTAGGAACC (SEQ ID NO:7); RT5', ACCT ACACCTGTCAACATAATTGG (SEQ ID NO:8); and RT3', GATAAATTTGATATGTCCA TTG (SEQ ID NO:9).

Pseudotype virus production and infection. The vesicular stomatitis virus glycoprotein (VSV-G)-pseudotyped HIV-1 virus was produced as described previously (Pierson, et al., 2002). Briefly, 293T cells were cotransfected with wild-type or recombinant pNL4-3-DE-GFP and pVSV-G by use of Lipofectamine 2000 (Invitrogen) according to the manufacturer's instructions. Four hours after transfection, the medium was replaced with RPMI 1640 (Invitrogen) supplemented with 10% fetal bovine serum (Gemini) and 50% normal human serum (Gemini). Where appropriate, protease inhibitors (PIs) were added at this step. Supernatants containing VSV-G-pseudotyped HIV-1 virus were collected 48 h after transfection. Cell debris was removed from the supernatant by spinning at 450×g for 5 min and filtering through Steriflip filters (Millipore). Viral supernatants were then used for infection or stored at −80° C.

The viral supernatants were standardized based on the number of GFP-positive transfected 293T cells per unit volume, which was calculated as the concentration of 293T cells times the fraction of GFP-positive 293T cells at 24 h post transfection. Specific volumes of viral supernatants that were equivalent to a given number of virus-producing 293T cells were used to infect $0.5 \times 10^6$ Jurkat cells. Jurkat cells are a transformed human T cell line. The infection was induced by mixing each viral supernatant with $0.5 \times 10^6$ washed Jurkat cells in a constant final volume and spinning at 1,800×g at 30° C. for 2 h. Where appropriate, PIs, nucleoside analogue RT inhibitors (NRTIs), and normucleoside RT inhibitors (NNRTIs) were added during the infection and maintained throughout the culture. When NRTIs were used, the Jurkat cells were precultured in the presence of NRTIs for 16 h before infection in order to allow for intracellular phosphorylation to produce the active triphosphate forms of the drugs. After the 2-h spin infection, Jurkat cells were washed, resuspended in 2 ml of culture medium (RPMI 1640, 10% fetal bovine serum, 50% human serum), and incubated in 24-well plates at 37° C. for 48 h before analysis by flow cytometry.

Analysis of Jurkat cells infected with recombinant NL4-3-DE-GFP. For quantification of the replication of recombinant HIV-1 containing patient-derived gag-pol sequences, the percentage of infected Jurkat cells was measured. Jurkat cells were collected at 48 h post infection, washed, and fixed with 1% paraformaldehyde in phosphate-buffered saline for 30 min on ice. Flow cytometry was performed in a FACScan instrument (Becton Dickinson) and analyzed with CellQuest software (Becton Dickinson). Replication was quantified as the percentage of GFP-positive Jurkat cells after gating for live cells.

The 50% inhibitory concentration ($IC_{50}$) for each antiretroviral drug was determined by drug titration in this system. Minimum and maximum concentrations in plasma (Cmin and Cmax, respectively) for current antiretroviral drugs were obtained from the manufacturers and from the Micromedex database. Viral isolates were compared with respect to the replication capacity index, defined as the ratio of the fraction of target cells infected by the test isolate to the fraction of target cells infected by the reference wild-type NL4-3 clone in the absence of drugs, and the drug resistance index, defined as the ratio of the fraction of infected target cells in the presence of drugs to the fraction of infected target cells in the absence of drugs. The replication index was defined as the product of the replication capacity index and the drug resistance index. This value sums the two effects on a log scale and represents the total treatment benefit.

Rationale. The goal of this study was to compare the relative contributions of two treatment effects that benefit patients with drug resistance, namely the residual susceptibility of resistant viruses to inhibition by drug combinations and the selection pressure to maintain drug-resistant mutants with reduced replication capacities relative to the wild-type virus. Both effects reduce viral replication relative to the replication of wild-type virus in the absence of drugs, and thus both effects can be measured on the same scale in replication assays.

However, because of the potent inhibitory effects of multiple antiretroviral drugs used in combination, an assay with a wide dynamic range is essential. To this end, patient-derived gag-pol sequences, including sequences for protease and part of RT, were cloned into a novel HIV-1 vector carrying an ER-retained form of the fluorescent reporter GFP. This vector was used to generate pseudotyped virus particles that were used to infect $CD4^+$ T cells in the presence or absence of relevant drug combinations. In this system, viral replication can be measured over a wide dynamic range (4 logs) by the detection of infection at the single-cell level by flow cytometry.

Example 1

Production and characterization of a recombinant HIV-1 vector for single-cell phenotypic analysis. A portion of the env gene of the pNL4-3 proviral clone was replaced with an inframe insert encoding an enhanced form of GFP followed by in-frame codons for a KDEL (SEQ ID NO: 14) ER retention signal (Munro, et al., 1987) and a stop codon (FIG. 1A). The resulting vector, pNL4-3-DE-GFP, expresses an Env-GFP fusion protein that is translocated into the ER and retained there, resulting in the accumulation of high levels of intracellular GFP. The expression of GFP fused to a virion structural protein under transcriptional control of the HIV-1 long terminal repeat allowed a high level of expression in infected cells.

After cotransfection of 293T cells with the Env-negative pNL4-3-DE-GFP vector and a construct encoding VSV-G, VSV-G-pseudotyped HIV-1 virions were harvested and used to infect cells of the $CD4^+$ human T-cell Jurkat line in single round infections. FIG. 1B shows the results of infection of Jurkat cells with pseudotyped viruses carrying gag-pol sequences from the reference HIV-1 clone NL4-3 or from a patient isolate. Infected cells were readily detected by flow cytometry. By confocal microscopy, infected cells showed bright perinuclear staining, consistent with ER localization of the Env-GFP fusion protein (not shown). Because of the high levels of fluorescence in infected cells and the low background fluorescence (<0.01%) (FIG. 1B), the dynamic range of the assay is limited principally by the number of cells analyzed. In this system, a dynamic range of up to 4 logs can be readily achieved.

Example 2

Measurement of replication capacity. In order to compare the replication capacities of viruses with different gag-pol sequences, it was necessary to normalize viral stocks to control for differences in transfection efficiency. Transfection supernatants could not be normalized based on p24 levels in the supernatants since virus release is influenced by protease (Kaplan, et al., 1994) and since Gag cleavage to generate p24 is dependent on protease activity and can be influenced by protease mutations (Zennou, et al., 1998). Similarly, RT assays could not be used since drug resistance mutations in RT can reduce the function of the enzyme (Back, et al., 1996).

Stocks of pseudotyped virus were normalized based on the number of transfected cells, as determined by GFP expression. GFP expression was measured in an aliquot of transfected 293T cells to determine how many cells were successfully transfected with the vectors and were capable of expressing viral genes and thus producing pseudovirions. CD4+ T cells were infected with normalized viral supernatants representing fixed numbers of virus-producing cells, and the number of infected target cells, as measured by flow cytometry, was used as a readout for viral replication. This approach ensures that the efficiency of every step in the viral life cycle, including viral assembly, release, maturation, entry, reverse transcription, integration, and viral gene expression, is captured in the measurement of replication capacity.

A direct linear relationship was observed between the number of target cells infected and the input amount of pseudotyped viral stock representing a known number of virus-producing cells (FIG. 1C). This linear relationship was observed for all isolates tested, including wildtype and drug-resistant isolates from patients in the presence and absence of drugs. This allowed use the number of infected cells as a direct readout for viral replication. Measurements of replication capacity by this method showed a very low variation coefficient (0.05±0.02).

Example 3

Effective concentration and estimated in vivo potency for individual drugs. To demonstrate the usefulness of this phenotypic assay for measuring the inhibition of viral replication by antiretroviral drugs, the concentrations of protease and RT inhibitors needed to inhibit the replication of the reference wild-type NL4-3 clone in this system were determined by drug titration. In order to make the system mimic in vivo conditions as closely as possible, assays with 50% human serum to account for the propensity of some antiretroviral drugs to bind to plasma proteins were performed.

PIs were added 4 h after transfection and were maintained in the culture during virus production and maturation and the infection of target cells. Target cells were preincubated with NRTIs for 16 h to allow these drugs to be converted to active triphosphate forms via intracellular phosphorylation. Longer preincubation times (24 h) did not further increase the inhibition by NRTIs. NRTIs, PIs, and NNRTIs were added to the viral supernatants during spin infections and were maintained in the culture medium during the subsequent incubation.

Figure 2:
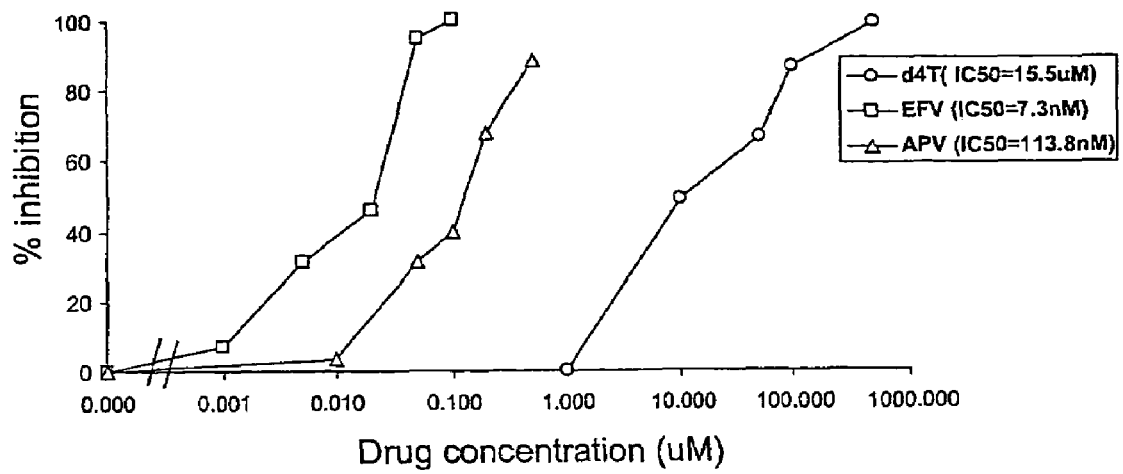
FIG. 2. Measurement of viral susceptibility to antiretroviral drugs using the pNL4-3-DE-GFP-derived pseudoviruses. The ability of pseudovirions carrying wild-type NL4-3 gag-pol sequences to infect Jurkat cells was measured in the presence of increasing concentrations of the NRTI d4T, the NNRTI EFV, and the PI APV. APV was added to cultures of virus-producing cells beginning 4 hours after transfection and was maintained throughout the course of viral assembly, release, maturation, and spin inoculation into the target cells. d4T was added to target cells beginning 16 h before infection and was maintained in all steps thereafter. EFV was added at the time of spin infection and was maintained thereafter. The IC50 for each drug was calculated by fitting data to the median-effect pharmacokinetic model.

FIG. 2 shows typical titration curves for representative drugs from the three major classes of antiretroviral drugs, the NRTI stavudine (d4T), the NNRTI efavirenz (EFV), and the PI amprenavir (APV). Each drug produced the expected sigmoidal dose-response curve for the inhibition of viral replication. The $IC_{50}$ values were calculated from the titration curves dosing. Potency for the in vivo antiretroviral was estimated by fitting of a median-effect pharmacokinetic model. Differences in potency revealed by this analysis take on additional significance when viewed in the context of the different Cmin and Cmax values achieved by each drug under normal dosing.

Figure 3:
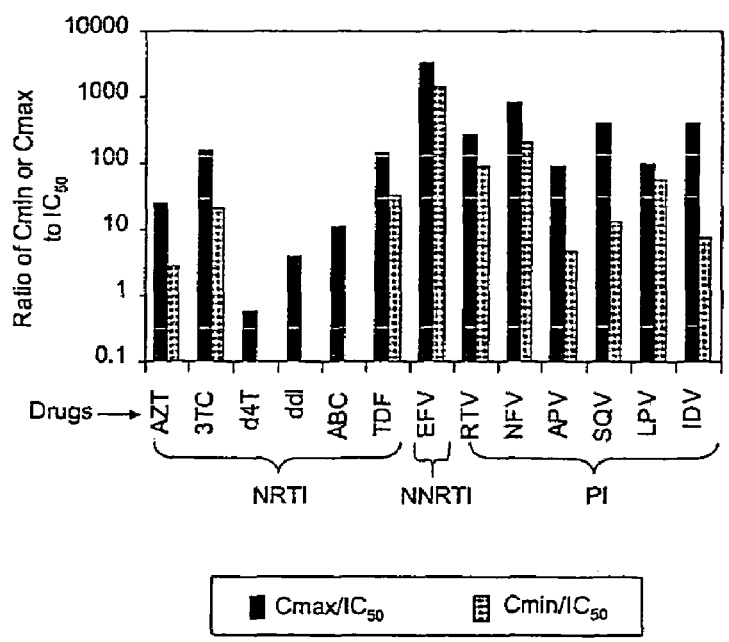
FIG. 3. Ratios of Cmin and Cmax to $IC_{50}$ for individual antiretroviral drugs. The in vitro $IC_{50}$ was measured for each drug by using pseudoviruses carrying the reference NL4-3 sequence as described in FIG. 3. The ratios between published $C_{max}$ and $C_{min}$ values and the $IC_{50}$ for each drug are plotted. ABC, abacavir; TDF, tenofovir disoproxil fumarate; RTV, ritonavir; NFV, nelfinavir; SQV, saquinavir; LPV, lopinavir; IDV, indinavir FIG. 4. Simultaneous measurement of susceptibility to 3TC and replication capacity for different HIV-1 clones. Pseudovirions carrying patient-derived isolates and NL4-3 gag-pol sequences were used to infect Jurkat cells in the presence of the indicated concentrations of 3TC. Drug resistance mutations in the protease and RT of patient derived HIV-1 clones are shown in Table 2.

In vivo potency for the antiretroviral drugs in current use was estimated by calculating the ratios of published Cmin and Cmax values to the $IC_{50}$ values measured in this system (FIG. 3). Consistent with the clinical potency of the NNRTI EFV, this drug demonstrated extraordinary potency in that even the Cmin was >1,000-fold higher than the $IC_{50}$ in this assay. The PIs were relatively potent, with Cmin values that were at least 10-fold higher than the $IC_{50}$ values (except for APV and indinavir). For some of the NRTIs, particularly d4T and didanosine (ddI), $C_{max}$ values were close to or below the $IC_{50}$ values.

Example 4

Inhibition by multiple drugs in combination. In infected individuals undergoing HAART, HIV-1 evolves in the simultaneous presence of multiple antiretroviral drugs. Most phenotypic assays measure the capacity of viruses to replicate in the presence of individual drugs. Such assays, therefore, do not take into account the complex synergistic and antagonistic interactions between antiretroviral drugs in the setting of HAART.

Antiretroviral drugs can affect each other's efficacies at the level of absorption, systemic metabolism and elimination, prodrug activation, and the targeted enzymatic reaction (Lederman, et al., 2000). Interactions affecting absorption and metabolism alter drug concentrations in the blood and are compensated for clinically by adjustments in dosage so that optimal blood levels are achieved. Interactions affecting prodrug activation and enzyme inhibition occur at the level of the target cells and can be directly assessed by using in vitro assays such as the one described here.

Table 1 shows that zidovudine (AZT) and d4T strongly antagonize each other in this system, as previously reported for other in vitro (Hoggard, et al., 1997) and in vivo (Havlir, et al., 2000) assays. The inhibition of viral replication observed in the presence of both drugs is much less than expected based on the fraction product principle (Webb, 1963). This antagonism reflects the fact that both are thymidine analogue prodrugs that share the same intracellular phosphorylation pathway. These results suggest that drug interactions that are operative in target cells can be accurately modeled in this in vitro system.

TABLE 1

Measurement of intracellular drug interactions between AZT and d4T

| Drug treatment[a] | % GFP-positive target cells[b] | Mean % GFP-positive target cells | Drug resistance index[c] | P value for antagonism[d] |
|---|---|---|---|---|
| No drug | 18.62 | 20.09 | | |
| | 24.16 | | | |
| | 20.08 | | | |
| | 17.49 | | | |
| 10 µM AZT | 7.61 | 7.15 | 0.356 | |
| | 6.70 | | | |
| | 7.59 | | | |
| | 6.71 | | | |
| 10 µM d4T | 6.83 | 6.54 | 0.325 | |
| | 7.04 | | | |
| | 5.74 | | | |

TABLE 1-continued

Measurement of intracellular drug interactions between AZT and d4T

| Drug treatment[a] | % GFP-positive target cells[b] | Mean % GFP-positive target cells | Drug resistance index[c] | P value for antagonism[d] |
|---|---|---|---|---|
| 10 µM AZT plus 10 µM d4T | 7.14<br>8.76<br>5.78<br>7.33 | 7.25 | 0.361 | <0.001 |

[a]Jurkat cells were infected in replicate with pseudotyped reporter viruses carrying the NL4-3 gag-pol sequence in the presence of the indicated drug(s). The drug(s) was added to target cells 16 h before infection and was maintained throughout the experiment.
[b]Measured 48 h after infection.
[c]The drug resistance index is the ratio of the measured replication in the presence of drug(s) to that in the absence of drugs.
[d]Antagonism is scored according to the fraction product principle. $f_0$ represents the fraction of infected cells in the absence of drug; $f_{AZT}$ and $f_{d4T}$ represent the fractions of infected cells in the presence of 10 µM AZT and 10 µM d4T, respectively; $f_{(AZT+d4T)}$ represents the fraction of infected cells in the presence of the combination of 10 µM AZT and 10 µM d4T. If AZT and d4T function independently, then $f_{(AZT+d4T)}/f_0$ should equal $f_{(AZT+d4T)}/f_0 \times f_{d4T}/f_0$; if $f_{(AZT+d4T)}/f_0 > f_{AZT}/f_0 \times f_{d4T}/f_0$, then there is antagonism, and if $f_{(AZT)}/f_0 \times f_{d4T}/f_0 < f_{AZT}/f_0 \times f_{d4T}/f_0$, then there is synergism. $f_0$, $f_{AZT}$, $f_{d4T}$, and $f_{(AZT+d4T)}$ were measured as the means of three or four replicates for each condition.
The P value is of the coefficient for the interaction term in $(f_{(AZT)}/f_0) \times \ln (f_{d4T}/f_0)$ being equal to zero in a multilinear regression.

Example 5

Analysis of drug susceptibility and replication capacity. As described above, the percentage of target cells infected by a standardized viral inoculum can be used as a direct readout for the replication of viruses with different gag-pol inserts. Thus, the abilities of patient derived resistant HIV-1 isolates and wild-type HIV-1 to replicate could be compared in the absence and presence of drugs.

To facilitate these comparisons, a replication capacity index, a drug resistance index, and a replication index were defined. A replication capacity index of <1 indicates a diminished replication capacity relative to that of the reference virus, NL4-3. A drug resistance index of <1 indicates susceptibility to the drug. The replication index, defined as the product of the replication capacity index and the drug resistance index, sums the two effects on a log scale and represents the total treatment benefit.

Figure 4:
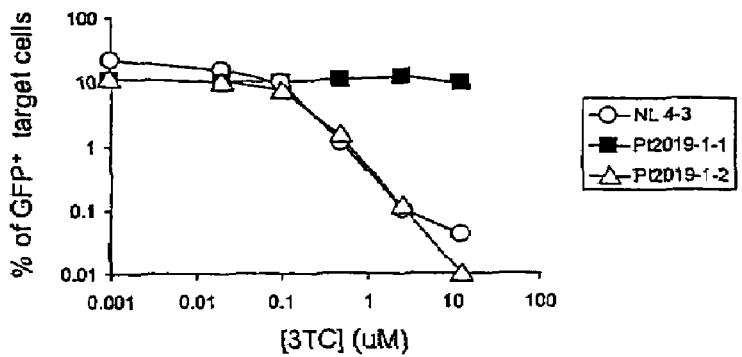

For example, FIG. 4 compares the abilities of pseudoviruses carrying two patient-derived drug-resistant HIV-1 sequences to replicate in the presence and absence of the NRTI lamivudine (3TC). Both isolates are from the same patient and contain an almost identical spectrum of multiple drug resistance mutations in protease and RT, differing only by the presence of the characteristic 3TC resistance mutation M184V in one isolate. Both mutants exhibited a slightly diminished replication capacity relative to the wild-type NL4-3 virus. The replication capacity index of each was ~0.5. Yet, as expected from the genotype, the isolate containing the M184V mutation was fully resistant to 3TC (drug resistance index of 1 up to 2.5 µM 3TC and of 0.8 at 12.5 µM 3TC). The isolate lacking this mutation showed the same high degree of susceptibility to 3TC as wild-type NL4-3 over about 3 logs of inhibition (drug resistance index of <0.002 at 12.5 µM 3TC).

This result demonstrates that the phenotypic assay can simultaneously measure replication capacity and drug resistance for HIV-1 gag-pol isolates from patients. Interestingly, for the multidrug-resistant isolate pt2019-1-2 analyzed here, the magnitude of the decrease in replication capacity relative to that of NL4-3 in the absence of drugs was small compared to the profound degree of inhibition by 3TC of the viruses lacking the M184V mutation.

Example 6

Figure 5:
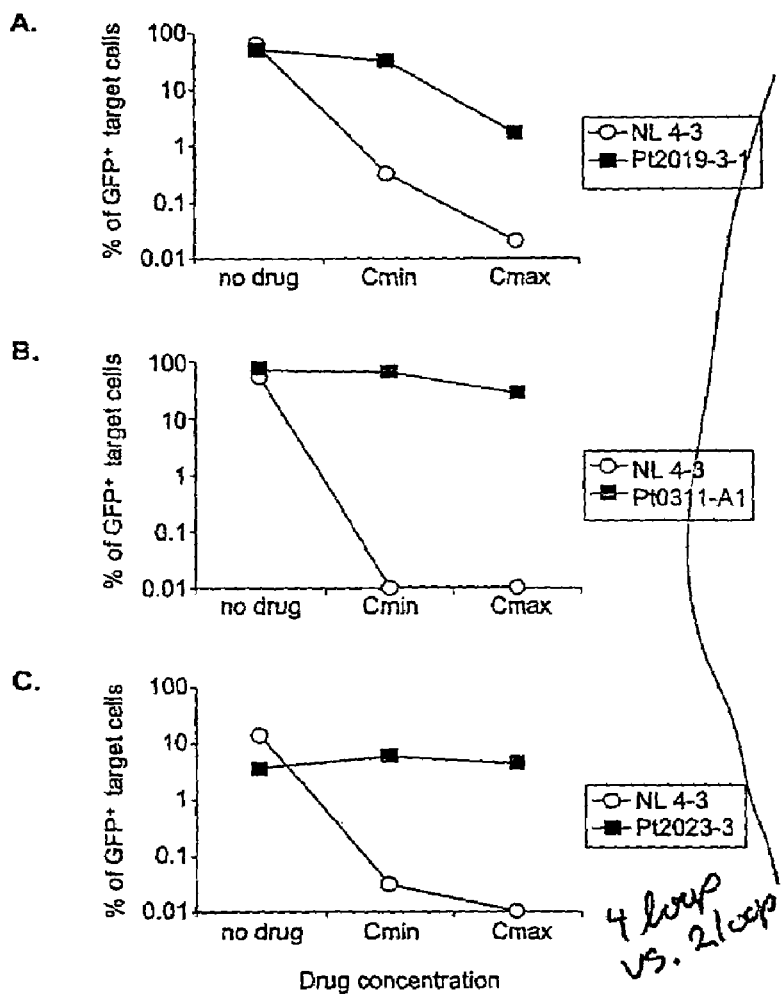
FIG. 5. Three different patterns of replication of drug-resistant HIV-1 clones reflecting differential contributions of residual drug susceptibility and reduced replication capacity. gag-pol sequences amplified from the plasma of patients failing therapy were used to generate pseudovirions that were then used to infect Jurkat cells in the absence of drugs and in the presence of failing drug combinations at the Cmin and Cmax of each drug. Drug resistance mutations present in each isolate are indicated in Table 2. The replication of each isolate was compared to that of the wild-type NLA-3 sequence.

Dissecting the benefits of nonsuppressive HAART into residual drug susceptibility and selection for resistant variants with diminished viral replication capacities. To demonstrate the utility of this assay for distinguishing residual suppression from diminished replication capacity, drug-resistant viruses from patients who were failing HAART regimens were analyzed. Three general patterns emerged (FIG. 5 and Table 2).

TABLE 2

Comparison of NL4-3 and patient-derived isolates with respect to replication capacity and drug resistance

| Isolate | Mutations[b] | | Replication Capacity Index[c] | Drug(s)[d] | Concn[e] (p.M) | Drug Resistance Index[f] | Replication Index[g] |
|---|---|---|---|---|---|---|---|
| | Protease | RT | | | | | |
| NL4-3 | Wild type | Wild type | 1 | 3TC | 12.5 | 0.002 | 0.002 |
| Pt2019-1-1 | L101, K20R, M361, M46L, I54V, L63A, A71V, 184V, 190M | M41L, M184V, H208Y, R211K, T215Y | 0.52 | 3TC | 12.5 | 0.8 | 0.42 |
| Pt2019-1-2 | L101, K20R, M361, I54V, L63A, A71V, 184V, L90M | M41L, H208Y, R211K, T215Y | 0.53 | 3TC | 12.5 | 0.001 | 0.00053 |
| NL4-3 | Wild type | Wild type | 1 | ddl, d4T, RTV, SQV | $C_{min}$<br>$C_{max}$ | 0.005<br>0.0003 | 0.005<br>0.0003 |
| Pt2019-3-1 | K20R, M361, M46L, I54V | M41L, M184V, H208Y, R211K, | 0.8 | ddl, d4T, RTV, SQV | $C_{min}$<br>$C_{max}$ | 0.63<br>0.03 | 0.504<br>0.02 |
| NL4-3 | Wild type | Wild type | 1 | d4T, 3TC, NFV | $C_{min}$<br>$C_{max}$ | 0.0002<br>0.0002 | 0.0002<br>0.0002 |
| Pt0311-A1 | D30N, N37D, M46I, L63P, A71T, V77I, N88D, I93L | M41L, D67N, V118I, M184V, L210W, R211K, T215Y | 1.34[h] | d4T, 3TC, NFV | $C_{min}$<br>$C_{max}$ | 0.94<br>0.39 | 1.26<br>0.52 |

TABLE 2-continued

Comparison of NL4-3 and patient-derived isolates with respect to replication capacity and drug resistance

| Isolate | Mutations[b] Protease | Mutations[b] RT | Replication Capacity Index[c] | Drug(s)[d] | Concn[e] (p.M) | Drug Resistance Index[f] | Replication Index[g] |
|---|---|---|---|---|---|---|---|
| NL4-3 | Wild type | Wild type | 1 | ddI, 3TC, ABC, EFV | $C_{min}$ | 0.005 | 0.005 |
|  |  |  |  |  | $C_{max}$ | 0.004 | 0.004 |
| Pt202-3 | Wild type | M41L, L74V, V75I, M184V, | 0.21 | ddI, 3TC, ABC, EFV | $C_{min}$ | 1.74 | 0.37 |
|  |  |  |  |  | $C_{max}$ | 1.31 | 0.28 |

Figure 6:
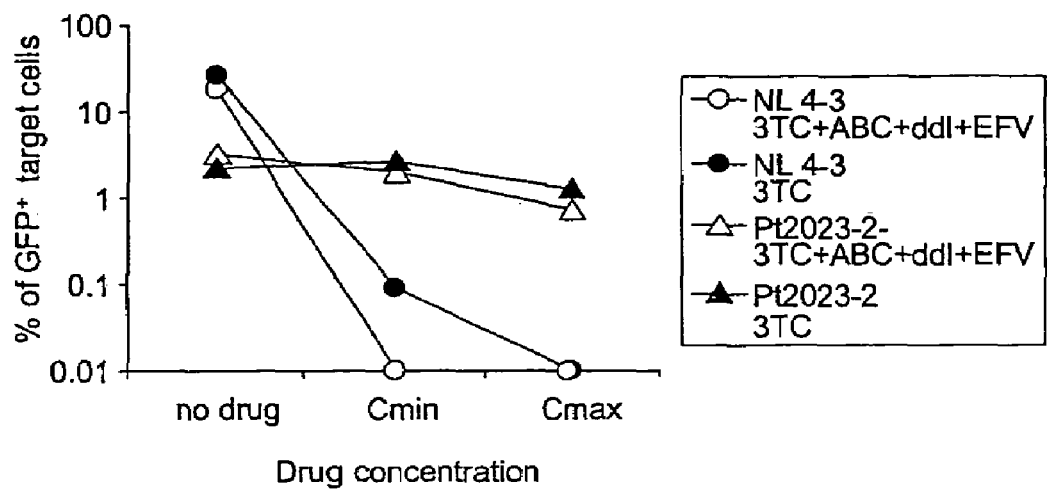
FIG. 6. In vitro demonstration of selection for a drug-resistant virus with reduced replication capacity by a simplifed regimen. The drug resistant virus analyzed for FIG. 5C was tesed for replication in the absence of drugs, in the presence of the failing regimen, and in the presence of a simplified regimen consisting of only 3TC. Replication of this isolate was compared to that of the wild-type NL4-3 sequence.

[a]The indicated patient-derived drug resistant isolates are shown in FIG. 5 and 6 and are compared with the reference NL4-3 sequence with respect to replication capacity and susceptibility to the indicated combinations of antiretroviral drugs. Isolates were obtained from the plasma or latent reservoir of patients on the relevant regimens.
[b]Characterized drug resistance mutations in protease and RT based on the International AIDS Society-USA compilation (11).
[c]The ratio of the replication capacity of the test isolate to the replication capacity of the reference wild-type NL4-3 clone in the absence of drugs.
[d]3TC, lamivudine; ddI, didanosine; d4T, stavudine; ABC, abacavir; EFV, efavirenz; RTV, ritonavir; SQV, saquinavir; NFV, nelfinavir.
[e]For drug combinations, each drug was used at its $C_{min}$ or $C_{max}$. The $C_{min}$ or $C_{max}$ values (pM) for the drugs used in this study are as follows: 3TC, 1.2 and 8.6; ddI, 0.04 and 6.78; d4T, 0.001 and 8.6; abacavir, 0.04 and 10.48; EFV, 8.57 and 13; ritonavir, 5.3 and 16; saquinavir, 0.3 and 9.3; nelfinavir, 1.74 and 6.97. $C_{min}$ and $C_{max}$ values were obtained from the Micromedex database and the manufacturer's package insert.
[f]The ratio of the measured replication of an HIV-1 isolate in the presence of the indicated drug regimen to replication in the absence of drugs.
[g]The product of the replication capacity index and the drug resistance index. The replication index is a measure of the capacity of the indicated isolate to replicate in the presence of the indicated drug regimen relative to the replication of the reference NL4-3 isolate in the absence of drug.
[h]This drug-resistant isolate replicated more efficiently than NL4-3 in the absence of drugs. If the replication capacity of this drug-resistant isolate is compared to that of a wild-type isolate derived from the same patient, then the replication capacity index is 1.02.

In the first pattern, as shown in FIG. 5A, the resistant variant exhibited both a diminished replication capacity (replication capacity index of <1) and partial susceptibility to the drug combination being used (drug resistance index of <1), particularly when each drug was present at its Cmax. In this case, the defect in replication capacity relative to NL4-3 was slight (replication capacity index=0.8), indicating that the multiple mutations in protease and RT did not substantially decrease the capacity of these enzymes to function, possibly due to the compensatory effects of some of the secondary mutations. The replication of the wild-type clone NL4-3 was strongly inhibited by the fourdrug combination that constituted the patient's regimen at the time of virus isolation (drug resistance index=0.0003 at the $C_{max}$). The drug-resistant isolate was only partially inhibited (drug resistance index=0.63 at the $C_{min}$ and 0.03 at the $C_{max}$).

This partial inhibition represents the residual suppression of the drug-resistant virus by the regimen. Therefore, this HAART regimen may exert some control on viremia via both partial suppression and selection for isolates with diminished replication capacities.

In the second pattern, the patient-derived drug-resistant HIV-1 had a high replication capacity and minimal drug susceptibility. FIG. 5B shows data for a drug-resistant isolate with a replication capacity slightly higher than that of NL4-3. The replication capacity index relative to NL4-3 was 1.34. The replication capacity of this resistant virus was also compared to that of a wild-type virus isolated from the latent reservoir of the same patient. In this case, the replication capacity index was 1.02. Thus, this resistant isolate was highly fit despite the presence of several major drug resistance mutations (Table 2). In addition, the resistant isolate was only minimally suppressed by the drug combination (drug resistance index=0.94 and 0.39 at the Cmin and Cmax, respectively). Thus, for this isolate, treatment provides little benefit.

In the third pattern, shown in FIG. 5C, the patient-derived isolate was fully resistant to the HAART regimen (drug resistance index of ≧1 at both the Cmin and Cmax) yet it had a diminished replication capacity (replication capacity index=0.21) relative to that of the wild-type NL4-3 isolate. Therefore, if the patient harbors a wild-type virus that is similar in replication capacity to NL4-3, the HAART regimen may benefit the patient mainly by selecting for a resistant variant with a reduced replication capacity.

Example 7

In vitro analysis of partial treatment interruptions. In cases for which the clinical benefit of continued treatment is solely due to the selection for resistant variants with diminished replication capacities, as shown in FIG. 5C, the drug regimen could potentially be simplified to keep only the minimum number of drugs needed to select for the resistant variants over the wildtype virus. In this situation, none of the drugs would still exert any direct suppressive effect on the relevant viral enzymes; they would function only to suppress replication of the wild-type virus. This scenario can be modeled in the in vitro system described here.

For the particular example shown in FIG. 5C, the infections were repeated, using the original drug combination (ddI, abacavir, 3TC, and EFV) and 3TC alone (FIG. 6). As expected, the replication of the resistant virus was not affected, while the replication of the wild-type virus was strongly suppressed by 3TC alone, to almost the same extent as with the four-drug combination. Even in the presence of 3TC alone, the drug-resistant clone with a reduced replication capacity was still 30- to 100-fold more fit than the wild-type virus; thus, this analysis predicts that 3TC therapy alone is sufficient to maintain the resistant variant. Analysis of this kind could be used to find the simplest regimen that provides the best balance between reduced toxicity and prolonged suppression of wild-type virus.

REFERENCES

The following references to the extent they provide exemplary procedural or other details supplementary to those set forth herein, are specifically incorporated by reference.

Back, N. K., M. Nijhuis, W. Keulen, C. A. Boucher, E. B. Oude, A. B. van Kuilenburg, A. H. van Gennip, and B. Berkhout. 1996. Reduced replication of 3TC-resistant HIV-1 variants in primary cells due to a processivity defect of the reverse transcriptase enzyme. EMBO J. 15:4040-4049.

Barbour, J. D., T. Wrin, R. M. Grant, J. N. Martin, M. R. Segal, C. J. Petropoulos, and S. G. Deeks. 2002. Evolution of phenotypic drug susceptibility and viral replication capacity during long-term virologic failure of protease inhibitor therapy in human immunodeficiency virus-infected adults. J. Virol. 76:11104-11112.

Baron, et al. (2004).

Blankson, J. N., D. Persaud, and R. F. Siliciano. 2002. The challenge of viral reservoirs in HIV-1 infection. Annu. Rev. Med. 53:557-593.

Deeks, S. G. 2001. Durable HIV treatment benefit despite low-level viremia: reassessing definitions of success or failure. JAMA 286:224-226.

Deeks, S. G., T. Wrin, T. Liegler, R Hoh, M. Hayden, J. D. Barbour, N. S. Hellmann, C. J. Petropoulos, J. M. McCune, M. K. Hellerstein, and R M. Grant. 2001. Virologic and immunologic consequences of discontinuing combination antiretroviral-drug therapy in HIV-infected patients with detectable viremia. N. Engl. J. Med. 344:472-480.

Finzi, D., M. Hermankova, T. Pierson, L. M. Carruth, C. Buck, R. E. Chaisson, T. C. Quinn, K. Chadwick, J. Margolick, R. Brookmeyer, J. Gallant, M. Markowitz, D. D. Ho, D. D. Richman, and R. F. Siliciano. 1997. Identification of a reservoir for HIV-1 in patients on highly active antiretroviral therapy. Science 278:1295-1300.

Havlir, D. V., N. S. Hellmann, C. J. Petropoulos, J. M. Whitcomb, A. C. Collier, M. S. Hirsch, P. Tebas, J. P. Sommadossi, and D. D. Richman. 2000. Drug susceptibility in HIV infection after viral rebound in patients receiving indinavir-containing regimens. JAMA 283:229-234.

Havlir, D. V., C. Tierney, G. H. Friedland, R. B. Pollard, L. Smeaton, J. P. Sommadossi, L. Fox, H. Kessler, K. H. Fife, and D. D. Richman. 2000. In vivo antagonism with zidovudine plus stavudine combination therapy. J. Infect. Dis. 182:321-325.

Hermankova, M., S. C. Ray, C. Ruff, M. Powell-Davis, R. Ingersoll, R. T. D'Aquila, T. C. Quinn, j D. Siliciano, R. F. Siliciano, and D. Persaud. 2001. HIV-1 drug resistance profiles in children and adults with viral load of <50 copies/ml receiving combination therapy. JAMA 286:196-207.

Hoggard, P. G., S. Kewn, M. G. Barry, S. H. Khoo, and D. j Back. 1997. Effects of drugs on 2',3'-dideoxy-2',3'-didehydrothymidine phosphorylation in vitro. Antimicrob. Agents Chemother. 41:1231-1236.

Katzenstein, D. A., R. J. Bosch, N. Hellmann, N. Wang, L. Bacheler, and M. A. Albrecht. 2003. Phenotypic susceptibility and virological outcome in nucleoside-experienced patients receiving three or four antiretroviral drugs. AIDS 17:821-830.

Kozal, et al. (1996).

Lederman, M. M., and H. Valdez. 2000. Immune restoration with antiretroviral therapies: implications for clinical management. JAMA 284:223-228.

Lucas, G. M., R. E. Chaisson, and R. D. Moore. 1999. Highly active antiretroviral therapy in a large urban clinic: risk factors for virologic failure and adverse drug reactions. Ann. Intern. Med. 131:81-87.

Munro, S., and H. R. Pelham. 1987. A C-terminal signal prevents secretion of luminal ER proteins. Cell 48:899-907

Nijhuis, M., S. Deeks, and C. Boucher. 2001. Implications of antiretroviral resistance on viral fitness. Curr. Opin. Infect. Dis. 14:23-28.

Perelson, A. S., P. Essunger, Y. Cao, M. Vesanen, A. Hurley, K. Saksela, M. Markowitz, and D. D. Ho. 1997. Decay characteristics of HIV-1-infected compartments during combination therapy. Nature 387:188-191.

Pierson, T. C., Y. Zhou, T. L. Kieffer, C. T. Ruff, C. Buck, and R. F. Siliciano. 2002. Molecular characterization of preintegration latency in human immunodeficiency virus type 1 infection. J. Virol. 76:8518-8531.

Ruff, C. T., S. C. Ray, P. Kwon, R. Zinn, A. Pendleton, N. Hutton, R. Ashworth, S. Gange, T. C. Quinn, R. F. Siliciano, and D. Persaud. 2002. Persistence of wild-type virus and lack of temporal structure in the latent reservoir for human immunodeficiency virus type 1 in pediatric patients with extensive antiretroviral exposure. J. Virol. 76:9481-9492.

Shulman, N. S., M. D. Hughes, M. A. Winters, R. W. Shafer, A. R. Zolopa, N. S. Hellmann, M. Bates, J. M. Whitcomb, and D. A. Katzenstein. 2002. Subtle decreases in stavudine phenotypic susceptibility predict poor virologic response to stavudine monotherapy in zidovudine-experienced patients. J. Acquir. Immune Defic. Syndr. 31:121-127.

Siliciano, J. F., Kajdas, D. Finzi, T. C., Quinn, K. Chadwick, J. B. Margolick, C., Kovacs, S. J. Gange, and R. F. Siliciano. 2003. Long-term follow-up studies confirm the stability of the latent reservoir for HIV-1 in resting CD4(+) T cells. Nat. Med. 9:727-728.

Simon, V., N. Padte, D. Murray, J. Vanderhoeven, T. Wrin, N. Parkin, M. Di Mascio, and M. Markowitz. 2003. Infectivity and replication capacity of drug-resistant human immunodeficiency virus type 1 variants isolated during primary infection. J. Virol. 77:7736-7745.

Webb, J. L. 1963. Enzymes and metabolic inhibitors, p. 66-79, 487-512. Academic Press, New York, N.Y.

What is claimed is:

1. A human immunodeficiency virus (HIV) vector comprising in frame gag-pol and an endoplasmic reticulum (ER) retained fluorescent protein/C-terminal signal sequence in frame with a stop codon inserted into the HIV env at a position about 125 bp from the env N-terminus replacing an env restriction fragment deletion.

2. The vector of claim 1 wherein the restriction fragment deletion is a KpmI-NheI deletion.

3. The vector of claim 1 wherein the HIV is HIV-1.

4. The vector of claim 1 wherein the stop codon is selected from the group consisting of TAA, TAG and TGA.

5. The vector of claim 1 wherein the fluorescent protein is selected from the group consisting of reef coral fluorescent proteins, *Aequorea victoria* fluorescent proteins, green fluorescent protein and variants thereof.

6. The vector of claim 1 wherein the fluorescent protein is green fluorescent protein (GFP).

7. The vector of claim 1 wherein the C-terminal signal sequence is KDEL (SEQ ID NO: 14) or HIEL (SEQ ID NO: 15).

8. The vector of claim 1 wherein the C-terminal signal sequence is KDEL (SEQ ID NO: 14).

9. The vector of claim 1 wherein the gag-pol is a heterologous gag-pol obtained from a human HIV patient.

10. The vector of claim 9 wherein the heterologous gag-pol is obtained from a human HIV patient treated with highly active anti-retroviral therapy (HAART).

11. A cell transformed with the vector of claim 1.

12. A cell line prepared from the vector of claim 1.

13. The vector of claim 10 wherein the HAART comprises a cocktail of drugs selected from the group consisting of zalcitabine (ddC), didanosine (ddI), amprenavir (AVP), Ritonavir (RTV), abacavir (ABC), tenofovir disoproxil fumarate, (TDF), nelfinavir (NFV), saquinavir (SQV), lopinavir (LPV) and indinavir (IDV)

14. A pseudotyped human immunodeficiency virus (HIV) comprising VSV-G that incorporates the vector of claim 1.

15. A tool for evaluation of human immunodeficiency virus (HIV-1) drug treatment regimens, said tool comprising a vesicular stomatitis virus glycoprotein (VSV-G)-pseudotyped HIV-1 comprising a fluorescent fusion protein/C-terminal signal sequence inserted at an env deletion which is positioned within 125 bp of the env N-terminus, wherein said terminal signal prevents secretion of expressed fluorescent fusion protein from the endoplasmic reticulum of a cell infected with the pseudotyped HIV-1.

16. The tool of claim 15 wherein the C-terminal signal sequence is selected from the group consisting of KDEL (SEQ ID NO: 14) and HIEL (SEQ ID NO: 15).

17. The tool of claim 15 wherein the env deletion is a 1.5 kb ApaI-AgeI fragment.

18. A kit comprising in packaged or container form a human immunodeficiency virus (HIV) vector in acordance with claim 1, a vector harboring vesicular stomatitis virus glycoprotein, and directions for preparation of pseudotyped HIV.

19. The kit of claim 18 further comprising a population of viral producing cells selected from the group consisting of 293T, Jurkat and CD4+ cells.

20. The kit of claim 18 further comprising directions for determining HIV replication capacity.

21. The kit of claim 20 further comprising directions for assessing antiretroviral drug susceptibility in HIV-1 infected patients.

* * * * *